(12) United States Patent
Avrin et al.

(10) Patent No.: US 7,047,059 B2
(45) Date of Patent: May 16, 2006

(54) SIMPLIFIED WATER-BAG TECHNIQUE FOR MAGNETIC SUSCEPTIBILITY MEASUREMENTS ON THE HUMAN BODY AND OTHER SPECIMENS

(75) Inventors: William F. Avrin, San Diego, CA (US); Sankaran Kumar, San Marcos, CA (US); Peter V. Czipott, San Diego, CA (US); Walter N. Freeman, San Diego, CA (US); Hoke S. Trammell, III, San Diego, CA (US)

(73) Assignee: Quantum Magnetics, Inc, San Diego, CA (US)

( * ) Notice: Subject to any disclaimer, the term of this patent is extended or adjusted under 35 U.S.C. 154(b) by 758 days.

(21) Appl. No.: 09/818,700

(22) Filed: Mar. 27, 2001

(65) Prior Publication Data

US 2001/0029329 A1    Oct. 11, 2001

Related U.S. Application Data

(63) Continuation-in-part of application No. 09/135,890, filed on Aug. 18, 1998, now Pat. No. 6,208,884.

(51) Int. Cl.
*A61B 5/05*    (2006.01)

(52) U.S. Cl. .................. 600/409; 324/260; 324/207.21

(58) Field of Classification Search ................ 600/409, 600/407, 550, 547; 324/260, 207.21
See application file for complete search history.

(56) References Cited

U.S. PATENT DOCUMENTS

| | | | |
|---|---|---|---|
| 4,431,005 A | 2/1984 | McCormick | 128/656 |
| 4,709,213 A | 11/1987 | Padhrasky | 324/329 |
| 4,801,882 A | 1/1989 | Daalmans | 324/248 |

(Continued)

FOREIGN PATENT DOCUMENTS

DE    4436078    4/1996

(Continued)

OTHER PUBLICATIONS

G.M. Brittenham et al., Noninvasive Methods for Quantitative Assessment of Transfusional Iron Overload in Sickle Cell Disease, Seminars In Hematology, vol. 38, No. 1, Supp. 1, pp. 37-56 (Jan. 2001).

(Continued)

*Primary Examiner*—Eleni Mantis Mercader
(74) *Attorney, Agent, or Firm*—Armstrong Teasdale LLP

(57) ABSTRACT

A probe instrument using room-temperature sensor(s) that can measure variations in magnetic susceptibilities. The instrument has sufficient resolution to monitor paramagnetic materials in a human body, such as iron in a human liver, by noninvasively examining patients with iron-overload diseases. The instrument includes room temperature magnetic sensors, and detects the sample, that is, the tissue response to an alternating current field applied by an applied field coil. The applied field coil dimensions are chosen so that the applied field is optimized for maximum response from the liver while minimizing the effects due to the overlying abdominal tissue and at the same time not unduly increasing the sensitivity of the instrument to the lung. To overcome variations in the sensor output due to fluctuations in the applied field, change in the ambient temperature and mechanical relaxation of the instrument, the sensor-sample distance is modulated. The detector assembly is oscillated while the examined patient remains stationary. An improved water-bag technique is employed to eliminate background tissue response. The detector assembly forms part of a probe instrument for performing noninvasively the paramagnetic concentration of a patient.

105 Claims, 14 Drawing Sheets

U.S. PATENT DOCUMENTS

| | | | | |
|---|---|---|---|---|
| 4,827,217 | A | * | 5/1989 | Paulson .................... 324/248 |
| 4,969,469 | A | | 11/1990 | Mills ......................... 128/653 |
| 5,057,095 | A | | 10/1991 | Fabian ....................... 604/362 |
| 5,099,845 | A | | 3/1992 | Besz et al. ................. 128/653 |
| 5,105,829 | A | | 4/1992 | Fabian et al. .............. 128/899 |
| 5,107,862 | A | | 4/1992 | Fabian et al. .............. 128/899 |
| 5,188,126 | A | | 2/1993 | Fabian et al. .............. 128/899 |
| 5,190,059 | A | | 3/1993 | Fabian et al. .............. 128/899 |
| 5,233,992 | A | | 8/1993 | Holt et al. ............... 128/653.2 |
| 5,268,165 | A | | 12/1993 | Hedlund et al. ............... 424/9 |
| 5,305,751 | A | | 4/1994 | Chopp et al. .............. 128/654 |
| 5,322,682 | A | | 6/1994 | Bartzokis et al. ............. 424/9 |
| 5,353,807 | A | | 10/1994 | DeMarco .................... 128/772 |
| 5,384,109 | A | | 1/1995 | Klaveness et al. ............. 424/9 |
| 5,408,178 | A | | 4/1995 | Wikswo et al. ............. 324/201 |
| 5,425,382 | A | | 6/1995 | Golden et al. .............. 128/899 |
| 5,456,718 | A | | 10/1995 | Szymaitis ..................... 623/11 |
| 5,494,033 | A | | 2/1996 | Buchanan et al. .......... 128/653 |
| 5,558,091 | A | | 9/1996 | Acker et al. ................. 128/653 |
| 5,686,836 | A | | 11/1997 | Sasada et al. ............... 324/244 |
| 5,722,411 | A | | 3/1998 | Suzuki et al. |
| 5,735,279 | A | | 4/1998 | Klaveness et al. .......... 128/654 |
| 5,842,986 | A | | 12/1998 | Avrin et al. ................. 600/407 |
| 5,891,031 | A | * | 4/1999 | Ohyu .......................... 600/409 |
| 6,496,713 | B1 | * | 12/2002 | Avrin et al. ................. 600/409 |

FOREIGN PATENT DOCUMENTS

| | | |
|---|---|---|
| EP | 481211 | 4/1992 |
| GB | 2204133 | 11/1988 |
| WO | WO 94/04946 | 3/1994 |
| WO | WO 96/05768 | 2/1996 |
| WO | WO 00/57200 | 9/2000 |

OTHER PUBLICATIONS

C.M. Bastuscheck et al., Abstract: Detection of Iron Stores in the Human Body Using Magnetic Susceptibility, J. Appl. Phys. 52(3), one page, (Mar. 1987).

Farrell et al., "Magnetic Measurements of Human Iron Stores," IEEE Trans. On Magnetics, vol. Mag. 16, No. 5, pp. 818-823 (Sep. 1990).

C.M. Bastuscheck, "Technique for Measuring the AC Susceptibility of Portions of the Human Body or Other Large Objects," J. Appl. Phys. 58 (10), pp. 3896-3906 (1985).

F.M. Bryden, "Real Time Ultrasound in the Assessment of Intraocular Foreign Bodies," Eye 4, pp. 727-731 (1990).

E. Costa Monteiro, "Magnetic Measurement Techniques for Locating Foreign Bodies in Humans," Tenth International Conference on Biomagnetism, p. 314 (1996).

E.J. Finn, "Ferromagnetic Materials in Patients: Detection Before MR Imaging," Radiology 156, pp. 139-141 (1985).

R.E. Greenblatt, "Probablistic Reconstruction of Multiple Sources in the Bioelectromagnetic Inverse Problem," Inverse Problems 9, pp. 271-284 (1992).

E. Kanal, "Aneurysm Clip Testing for Ferromagnetic Properties: Clip Variability Issues," Radiology, pp. 576-578, (1995).

Mentor Corporation, "The Detector, Injection Port Detection System," Brochure, 6 pp., (1996).

D.N. Paulson, "Biomagnetic Susceptometer with SQUID Instrumentation," IEEE Transactions on Magnetics, vol. 27, No. 2, pp. 3249-3252 (1990).

D.N. Paulson, "The Hamburg Biosusceptometer for Liver Iron Quantification," Advances in Biomagnetism, pp. 497-500, (Date Unknown).

K. Sekihara, "Reduction of Brain Noise Influence in Evoked Neuromagnetic Source Localization Using Noise Spatial Correlation," Phys. Med. Biol. 39, pp. 937-946, (1993).

N. Sepulveda, "Magnetic Susceptibility Tomography for Three-Dimensional Imaging of Diamagnetic and Paramagnetic Objects," IEEE Transactions on Magnetics, vol. 30, No. 6, pp. 6062-5069, (1993).

F.G. Shellock, "Magnetic Resonance," Bioeffects, Safety and Patient Management, pp. 115-126, (1996).

N. Smith, "A High-Sensitivity Magnetoresistive Magnetometer," J. Appl. Phys. 69 (8), pp. 5082-5084 (1991).

B. Scholz, "Probability-Based Current Dipole Localization from Biomagnetic Fields," IEEE Transactions on Biomedical Engineering, vol. 41, No. 8, pp. 735-742 (1993).

W.M. Wynn, "Advanced Superconducting Gradiometer/Magnetometer Arrays and a Novel Signal Processing Technique," IEEE Transactions on Magnetics, vol. MAG-11, No. 2, pp. 701-707, (1974).

Brittenham et al., "Noninvasive Methods for Quantitative Assessment of Transfusional Iron Overload in Sickle Cell Disease", Seminars in Hematology, vol. 38, No. 1 Suppl. 1, Jan. 2001, pp. 37-56.

Farrell, et al., Magnetic Measurement of Human Iron Stores, Intermag 80, 1980 International Magnetics Conference, Boston, MA, USA, Apr. 21-24, 1980, vol. MAG-16. No. 5, Sep. 1980, pp. 818-823.

Bastuscheck, et al., Detection of Iron Stores in the Human Body Using Magnetic Susceptibility, Twenty-Sixth Annual Conference on Magnetism and Megnetic Materials, Dallas, TX, USA, Nov. 11-14, 1980, vol. 52, No. 3, pt. 2, Mar. 1981, p. 2581.

European Search Report, EP 05 00 2455, May 25, 2005.

* cited by examiner

MR sensor in low-field region between current sheets.

SIMPLIFIED WATER-BAG TECHNIQUE FOR MAGNETIC SUSCEPTIBILITY MEASUREMENTS ON THE HUMAN BODY AND OTHER SPECIMENS

CROSS-REFERENCE TO RELATED APPLICATION

This application is a continuation in part of parent application Ser. No. 09/135,890, filed 18 Aug. 1998, now U.S. Pat. No. 6,208,884, issued 27 Mar. 2001.

The U.S. Government has a paid-up license in this invention as provided for by the terms of Contracts Nos. N 43-DK-7-2250 and N44-DK-9-2309, both awarded by the National Institutes of Health.

BACKGROUND

1. Field of the Invention

This invention relates generally to an instrument using room temperature sensors that measure magnetic susceptibility variations in the body, and more particularly to such an instrument employing an improved water-bag technique to eliminate background tissue response.

2. Discussion of the Related Art

Millions of people suffer from diseases related to the metabolism of iron in the human body. Among these are Cooley's anemia (also known as thalassemia), sickle cell anemia, and hemochromatosis. Magnetic susceptibility measurements are an important non-invasive technique for measuring iron stores in the liver.

The need to obtain liver iron measurements is especially acute in the case of Cooley's anemia, or thalassemia. In this disease, where the blood is deficient in hemoglobin, patients must undergo blood transfusions in order to survive. These blood transfusions must be frequent (every 2 to 4 weeks). However, the repeated transfusions create a chronic iron overload with an abnormal buildup of iron in the liver, spleen, and heart. Sickle cell anemic patients undergoing frequent blood transfusions also suffer from liver iron overload. There are other conditions which affect liver iron concentration leading to the need for accurate, frequent, non-invasive measurements of iron in the liver and other areas of the body. This iron overload must be removed continually by chelation therapy, and iron stores must be monitored regularly to maintain the desired levels.

Biomagnetic susceptometry is a diagnostic procedure that involves noninvasive, radiation-free, direct, and accurate, measurement of the magnetic susceptibility of organs and tissue within a human or animal body. Biomagnetic susceptometry can be used to measure human iron stores contained in the liver.

Some existing instruments for such measurements are based on Superconducting Quantum Interference Devices (SQUIDs). However, they tend to be complex and expensive. SQUIDs based on High-Temperature Superconductors (HTS) could, in principle, reduce the cost of biomagnetic susceptometry. However, even at liquid-nitrogen temperatures, the operating costs would be higher than those of ordinary instruments operating at room temperature.

Presently available biomagnetic susceptometers have drawbacks in several different technical areas, as discussed below.

A key problem in the susceptometric liver iron measurement is the background signal produced by the magnetic susceptibility of the patient's body tissues. This tissue background signal can be many times larger than that due to iron in the liver, and it varies according to the shape of the patient's body. This variability can easily mask the magnetic susceptibility signal due to liver iron. To eliminate this background tissue response, the common practice is to put a water-bag between the sensor unit and the patient's body. See Farrell et al., Magnetic Measurement of Human Iron Stores, IEEE Transactions on Magnetics, Vol. Mag. 16, No. 5, pp. 818–823 (September 1980).

It is useful to first describe the conventional water-bag method and discuss some of its important limitations. The biomagnetic liver-iron measurement uses a sensor unit comprising a magnetic-field sensor and a coil that produces a magnetic field. When this sensor unit is sitting by itself in empty space, the magnetic sensor sees only the applied magnetic field from the coil. When the sensor unit is placed next to the patient's abdomen, the body tissues become slightly magnetized by the applied magnetic field, producing a small change in the magnetic field at the magnetic sensor. This change in magnetic field includes a contribution due to iron in the liver, plus a contribution from the magnetic susceptibility of the body tissues themselves.

The conventional water-bag method eliminates most of the error due to the susceptibility response of the body tissues. This method takes advantage of the fact that most body tissues have magnetic susceptibilities close to that of water. In existing biomagnetic susceptometer systems, the water-bag method works as shown in FIGS. 9A and 9B. Water-bag 91 is in the form of a flexible bellows which surrounds the lower end of sensor unit 92. Initially, the bellows is compressed as the patient's abdomen 93 is pressed up against the sensor unit. Then, the patient is moved down, away from the sensor unit (arrow 94), using a special non-magnetic, pneumatic table. As the patient is lowered, the bellows is filled with water, so that the magnetic susceptibility signal from the body tissues is replaced by an equivalent signal from the water in the water-bag. Hence, the magnetic sensor sees no net change in magnetic field due to the response of the body tissues. However, the iron in the liver has a susceptibility different from that of water. This difference in susceptibility produces a magnetic-field signal which changes as the patient's abdomen moves farther from the sensing unit.

This method has some disadvantages. First, in prior water-bag systems a special mechanism is required to add or withdraw water form the water-bag, as needed to maintain constant pressure. Second, noise may be introduced into the magnetic susceptibility measurement because of variations in the way the water-bag fills. Additionally, the need to fill and empty the water-bag makes it difficult to make rapid changes in the distance between the sensor and the patient. This limitation is not a problem with existing low temperature biomagnetic susceptometers, which use extremely stable sensors operating at liquid-helium temperatures. However, in a room-temperature instrument, the patient-sensor distance must be modulated continuously, at a frequency near 1 Hz, in order to cancel out the effects of temperature drift in the applied-field coils and magnetic sensors. It would be very difficult to fill and empty a water-bag at this rate. The conventional water-bag method also makes it difficult to scan the magnetic susceptometer along the body, in order to map out susceptibility variations within the body. This scanning capability is potentially useful in the liver iron measurement, as a means of determining the possible susceptibility response of tissues surrounding the liver, such as the lungs. Scanning measurements are also potentially useful in other applications such as the detection of ferromagnetic foreign bodies in a host.

An important issue in a room-temperature biomagnetic susceptometer is to minimize the noise caused by various things such as temperature drift and motion, among others, in the sensors used to detect the susceptibility response of the body.

SUMMARY OF THE INVENTION

Broadly speaking, this invention provides a practical method and apparatus for measuring variations of magnetic susceptibilities in body tissue and, in particular, iron concentration in a patient's liver. This invention obviates the need for cryogenically cooled SQUIDs by providing operational use at room temperature, making for much less expensive fabrication and use. The invention allows, generally, for measurements of variations of magnetic susceptibility in a patient and, in particular, for an accurate and inexpensive way of monitoring liver iron in patients. The magnetic susceptibility measurements made in accordance with the invention have sufficient resolution to monitor iron in the liver, when the instrument is placed external to the patient. In addition, certain improvements introduced in this invention are applicable to all types of magnetic susceptibility measurements.

The present invention concerns improvements in biomagnetic susceptometry techniques in at least three key areas: (1) the water-bag system used to minimize errors due to the background response of the patient's body tissues; (2) the type of sensors used to measure the magnetic susceptibility response in the room-temperature biomagnetic susceptometer; and (3) an electrostatic shielding technique to ensure that the sensor system responds to the magnetic susceptibility, and not the electrical capacitance of the patient's body.

This invention includes an improved version of the water-bag method. This new method is cheaper, simpler and more accurate than prior water-bag techniques. It reduces or eliminates certain measurement errors due to the shape of the water-bag. Most importantly, the new method permits more rapid modulation of distance between the sensor unit and the patient's body. This more rapid modulation greatly reduces or eliminates noise due to temperature variations in the measuring instrument, so that an inexpensive room-temperature sensor system can be employed instead of the expensive superconducting sensors used in previous biomagnetic susceptometers.

The magnetic sensor can be, but is not necessarily limited to, a magnetoresistive sensor (including giant magnetoresistive and spin-dependent tunneling sensors), a fluxgate magnetometer, a magneto-inductive sensor, or an induction coil, among others.

Research has shown that noise in magnetic susceptibility measurements can be improved by using multi-turn coils of wire to detect the magnetic susceptibility response. Such detection coils are referred to herein as induction coils because a changing or oscillatory magnetic field is detected by measuring the voltage induced in the coil due to the rate of change of the magnetic field.

The room-temperature biomagnetic susceptometer of this invention uses an oscillatory (AC) magnetic field to measure the magnetic susceptibility response of the body. In order to ensure that the susceptometer detects the magnetic susceptibility response, and not the electrical capacitance of the body, it is useful to ensure that the detection coil or other magnetic sensor is shielded from electric fields. The oscillatory applied magnetic field in the susceptometry measurement may have an amplitude of several gauss, and a frequency of several hundred hertz. This time-varying magnetic field may induce significant electric fields in the space surrounding the applied-field coil. These electric fields can be capacitively coupled to the detection coils or other magnetic sensors, producing a shift in the AC magnetic field measurement. When the sensor system is placed next to a patient's body, the electric fields may be distorted by the capacitance of the patient's body, producing a shift in the AC magnetic measurement, which depends on the presence of the body. This invention includes a method for preventing such effects, by shielding the magnetic sensors from electric fields.

The applied field coil dimensions are such that an applied field is optimized for maximum response from localized tissue areas, such as organs, in the body. For example, the instrument is particularly suitable for monitoring iron in the liver. For this application, the applied field coil dimensions are optimized to maximize the magnetic susceptibility response from the liver and minimize effects caused by the overlying abdominal tissue, while not unduly increasing the sensitivity of the probe instrument due to a lung being in close proximity to the liver.

To minimize noise introduced in the magnetic sensor due to fluctuations in the applied field, the applied field is canceled at the position of the sensor. Both the real and imaginary parts of the applied field are canceled. To overcome variations in the sensor output caused by changes in ambient temperature and mechanical relaxation of the instrument, the sensor-sample distance is modulated by oscillating the detector assembly. In contrast with conventional biomagnetic measurement instruments that use SQUID sensors, where a patient is moved relative to the instrument, the magnetic sensor of this invention is moved relative to the patient. In one embodiment, the detector assembly has an applied field coil fabricated on a printed circuit board (PCB) that is attached to a solid non-metallic support base, which in turn attaches to an oscillatory member which displaces the detector assembly when used for examining a patient. In an alternative embodiment, the applied field coil is wound on a cylindrical coilform which in turn attaches to an oscillatory member which displaces the detector assembly when used for examining the patient.

For field use a single medical instrument housing can incorporate the magnetic sensor control electronics a motor/crank rod (for example) arrangement for oscillatory movement of the distal end of the detector assembly, an applied AC field source signal generator, a lock-in amplifier, an audio amplifier, and an FFT spectrum analyzer or equivalent computer device for signal analysis.

A physician uses the probing instrument by positioning the distal end of the probe on a patient's abdomen and preferably oscillating the detector assembly over the organ, and specifically over the liver area in one particular use. The probe instrument then analyzes the observed signal and outputs data corresponding to material of interest, for example, paramagnetic material concentration such as iron when the instrument is used as an iron probing instrument.

BRIEF DESCRIPTION OF THE DRAWING

The objects, advantages and features of this invention will become readily apparent from the detailed description, when read in conjunction with the accompanying drawing, in which.

DETAILED DESCRIPTION OF THE PREFERRED EMBODIMENTS

Figure 1:
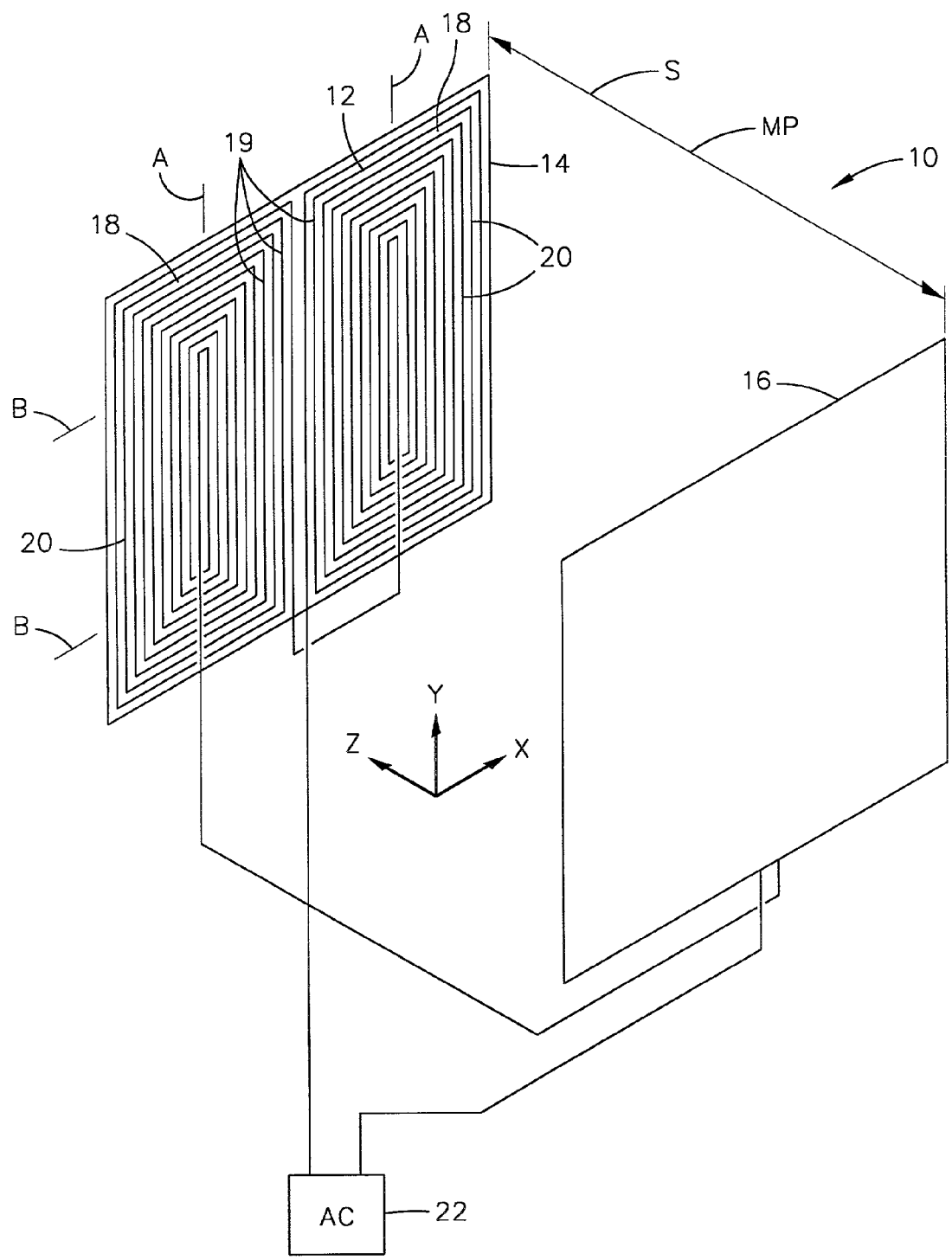
FIG. 1 schematically shows features of the applied field coils with a magnetic sensor of a magnetic susceptibility detector in accordance with the invention.

The present invention relates to a room-temperature medical probing instrument that measures variations of magnetic susceptibility. In particular, an exemplary liver probing instrument is described that has sufficient resolution to monitor liver iron in patients. The probe instrument of the invention can make magnetic susceptibility measurements with an uncertainty corresponding to a liver-iron concentration of about 30 micrograms per milliliter. This instrumental resolution is roughly ten times lower than the normal liver iron concentration, and thirty times lower than the iron concentration typically maintained in patients undergoing iron chelation therapy. Thus, an inexpensive room-temperature biomagnetometer, as discussed below, provides routine, cost-effective, non-invasive monitoring of iron in a patient's liver or other paramagnetic material as one device according to the invention.

The noise of the room-temperature instrument is small compared to the uncertainties (typically 200–500 micrograms/ml) that are actually achieved in liver-iron measurements on real patients. These uncertainties are caused mainly by the magnetic response of tissues between the liver and the abdominal surface. For a room temperature system, as for existing instruments based on SQUID sensors, this abdominal tissue effect, and not the noise in the magnetic sensors, determines the precision of liver-iron measurement. Because the crucial limitation in the sensitivity of the liver-iron measurement is imposed by the tissue response rather than the noise of the sensor itself, the somewhat higher noise of the room temperature functioning magnetic sensor compared to a SQUID is not a limiting factor in the performance of the instrument.

Performance of the room-temperature liver instrument depends on two critical issues:

1. The instrument has to be sensitive enough to see the small magnetic signals produced by the magnetic susceptibility of the liver; and
2. The liver susceptibility has to be determined accurately in the presence of the interfering signal produced by the slight magnetic susceptibility of the abdominal wall and other surrounding tissues such as the lung.

In magnetic susceptibility measurements, a magnetic field is applied, inducing a magnetization in the tissue area of interest. A small magnetic field produced by this sample magnetization is then detected using a magnetic sensor. At low applied fields, the sample magnetization is proportional to the intensity of the applied field and to the magnetic susceptibility of the sample, that is, the tissue.

In liver susceptometry, very weak susceptibilities are encountered. The difference in magnetic susceptibility between the liver and surrounding tissue is proportional to the liver iron concentration. The main iron compound stored in the liver has a susceptibility of approximately $1.6 \times 10^{-6}$ (in SI units) per milligram of iron per gram of wet liver tissue. Patients with iron overload typically have several milligrams of iron per gram of wet liver tissue. The instrumental noise of existing SQUID biosusceptometers corresponds to an uncertainty of about 20 micrograms per gram in liver iron concentration. Factors including uncertainty in the magnetic susceptibility of surrounding tissues contribute sources of systematic uncertainty in clinical liver measurements. Clinical measurements with existing SQUID-based instruments achieve uncertainties in the range of 0.2–0.5 milligrams of iron per gram of liver, which corresponds to a magnetic susceptibility resolution of $(3-7) \times 10^{-7}$ (SI Units).

To detect the weak magnetic response of the liver, there are two technical issues:

1. Minimization of noise in the detector magnetic-field sensors (and, to a lesser extent, the background noise from the environment) so that detection of the magnetic response can be performed without applying excessively large fields; and
2. Ensuring that the spurious signals due to the applied fields are small compared with the desired magnetic susceptibility signal.

Sensor noise requirements: To measure a given magnetic susceptibility, the applied field must be large enough and the noise from the magnetic sensor must be low enough so that the magnetic susceptibility response is much greater than the sensor noise. When using a room-temperature instrument, the applied field is limited by the need to avoid excessive ohmic heating in the applied field coils of the detector assembly. Excessive heat loads can induce thermal drifts in the geometry of the applied field coils. As discussed below, such drifts could affect the ability to suppress spurious signals due to the applied field. However, an applied magnetic field of roughly $10^{-3}$ T to a sample tissue does not incur excessive thermal drift effects.

If a field of $10^{-3}$ T is applied, and the magnetic field due to the response of the sample is $10^{-7}$ times the applied field, then the magnetic sensor noise must be less than $10^{-10}$ Tesla. Such noise requirements can readily be met using room-temperature functioning magnetic sensors. An induction coil sensor is employed in one embodiment of this invention. A fluctuating magnetic field in the vicinity of the induction coil sensor induces a electrical voltage across the sensor which can be measured to determine the strength of the fluctuating magnetic field. Another sensor that can be used in the invention is a magnetoresistive (MR) sensor with very low noise. Such sensors are commercially available from Honeywell, Philips, and other companies. The MR sensor operates on the principle that the resistance of particular magnetic materials (such as permalloy, an alloy of nickel and iron) is a function of the ambient magnetic field. Changes in the magnetic field result in changes in sensor resistance which can be measured and quantified. MR sensors developed by Kodak have noise spectral densities below 30 $pT/Hz^{1/2}$ at frequencies above 20–30 Hz. Similar noise levels are achieved by MR sensors commercially available from Honeywell. With a measurement bandwidth of 0.1 Hz (three seconds of data averaging) these sensors exhibit an RMS sensor noise of $10^{-11}$ Tesla. This noise level is ten times below an estimated liver iron signal of $10^{-10}$ Tesla. A variety of other sensor types could also meet the requirements of the present invention, including sensors based on magnetoresistance (such as magnetoresistive and giant magnetoresistance sensors and spin dependent tunneling sensors), as well as fluxgate magnetometers and magnetoinductive sensors.

To measure magnetic signals below 100 pT, care is required to reject magnetic noise from the environment. The requirements for noise rejection are less stringent in the present invention than in the existing SQUID biosusceptometers. The SQUID systems use DC magnetic fields, and produce a DC magnetic susceptibility response. These systems convert this DC magnetic response into a time-varying magnetic signal by moving the patient up and down at a frequency of 0.5 Hz. However, even with this modulation, the measurement takes place at a rather low frequency. At such frequencies, the background noise in many environments is relatively large.

The room-temperature system of this invention applies an AC magnetic field at a frequency between about 25 and about 2,000 hertz, and detects the magnetic response at the same frequency. At these frequencies, environmental background fluctuations are usually small, as long as noise peaks at harmonics of the power-line frequency are avoided.

Magnetic signal measurements needed for the liver probe instrument are $10^7$ times smaller than the field applied to a patient's body. In making such a measurement, technical issues include the stability of the applied magnetic field, the stability of the magnetic sensors, and the geometrical stability of the magnetic-field coils and sensor array.

In one embodiment the instrument of this invention is designed so that fluctuations of the current in the applied-field coil have only a negligible effect on the magnetic measurements. The invention uses a detector assembly whose applied field coil is geometrically configured such that almost no magnetic field occurs at a location where the magnetic sensor is positioned in relation to the applied field coils. If the magnetic sensor were exposed to the full amplitude of the applied field, then the current in the field coils would have to be stable to at least one part in $10^7$ to resolve the weak magnetic signals observed in biomagnetic susceptibility measurements. However, if the sensor observes only $10^{-4}$ of the field applied to the sample, the coil current can vary by as much as one part in $10^4$, and the corresponding variations in the magnetic measurements are then only $10^{-8}$ of the field applied to the sample.

In a second embodiment, the magnetic field response is detected by a set of two coils connected in series, equal in area, but oppositely wound, and oppositely spaced from the excitation coil on a cylindrical coilform in a first-order gradiometer configuration. Since the equal and opposite sensor coils are placed symmetrically with respect to the excitation coil, there is no net signal (voltage) induced in the sensor due to the excitation field. However, when one of the sensor coils is placed closer to the sample which is excited by the applied field, the sensor coil close to the sample preferentially detects more signal from the sample compared to the sensor coil farther away and therefore a net signal from the sample is induced in the sensor. The invention described herein combines a gradiometer sensor coil and an excitation coil with reciprocating motion of the detector in order to reduce noise due to thermal fluctuations and thereby enable the measurement of induced fields which have an amplitude of one part in ten million ($10^7$) of the applied field. A second innovation in this embodiment is the placement of an electrostatic shield around the sensor coil to eliminate the noise due to the electrostatic coupling between the sensor and the sample. One skilled in the art would know that the coil arrangement described above can be made using coil-forms of different diameters and lengths, as well as different coil separations. One skilled in the art would also know that the sensor coil can be made using other gradiometer configurations, including second-order or higher-order gradiometers, which will not sense the applied field but will preferentially detect the signal from the sample (for example, by using more than two sensor coils, symmetrically placed about the excitation coil).

Figure 2:
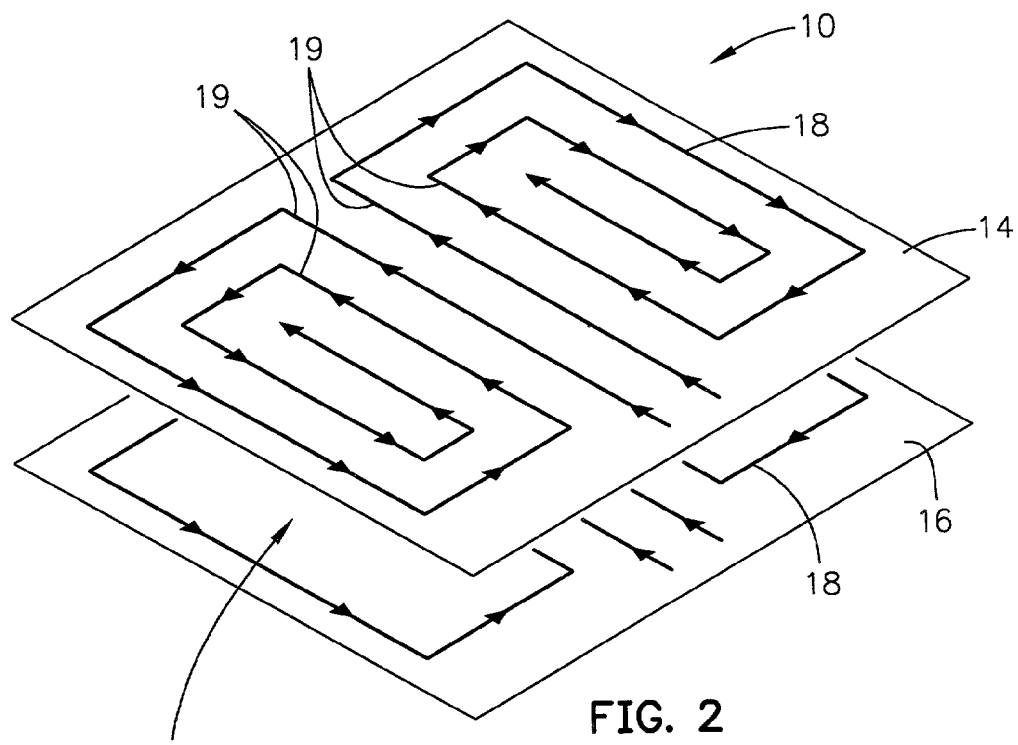
FIG. 2 is a perspective schematic view of the sensor field coils of the FIG. 1 configuration, showing the current directions.
Figure 3:
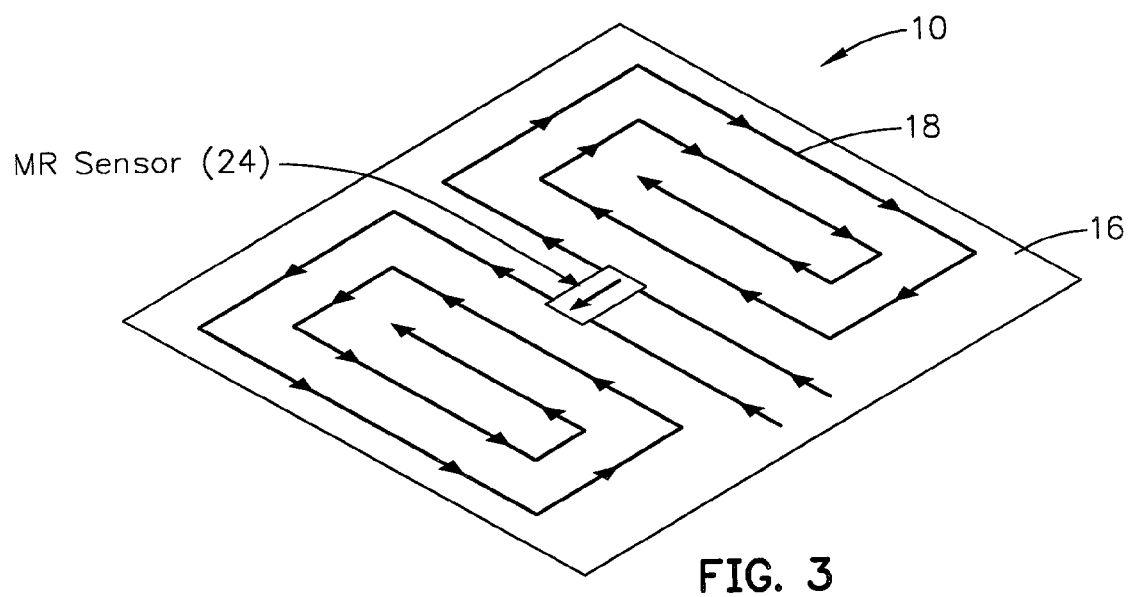
FIG. 3 is a view similar to FIG. 2, showing one planar coil-set with a magnetoresistive sensor.

FIGS. 1, 2 and 3 show an applied field coil and magnetic sensor design and system for determining FFB objects. Detector assembly 10 makes use of the technical principles discussed above. This detector assembly provides magnetic susceptibility measurement information available for the detection of retained ferromagnetic foreign body (FFB) object(s), that is, metallic objects inside human tissue, as a way of screening patients prior to magnetic resonance imaging (MRI) or other medical procedures.

The present invention teaches a different detector assembly configuration that improves the noise of the magnetic susceptibility measurements and optimizes response from the liver with respect to an interfering signal from overlying abdominal tissue and the lung. System components also include equipment for using magnetic measurement signals from the sensors to detect and locate ferromagnetic objects, and for distinguishing the signals of the target objects from other interfering magnetic fields.

FIGS. 1, 2, and 3 collectively show prior art detector assembly 10 which is intended to be placed near the body region to be screened. Applied field coils 18, when supplied with current from current signal generator 22, generate a time-varying applied magnetic field to the body. The magnetic material in the body region responds, providing a small magnetic field that is detected by sensor 24 (shown in FIG. 3) or array of sensors (not shown) positioned adjacent to the body region. Together, applied field coils 18 and sensor(s) 24 allow measurement of anomalies in the magnetic susceptibility of the body region being screened. In particular, the geometry of the applied field coils and the placement of the magnetic sensors are such that the interfering applied field experienced by magnetic sensor 24 is as small as possible. As discussed earlier, this arrangement reduces the interfering signal produced by the varying magnetic field. The detector assembly consisting of sensor(s) 24 and coils 18 can be stationary, or can be movable to generate a magnetic susceptibility anomaly map over the body part being screened. The intensity and the time dependence or frequency dependence of the magnetic susceptibility anomaly can be interpreted rapidly by a signal processor to reveal the location and size of ferrous metallic objects retained within the screened body region.

The applied magnetic field may be several orders of magnitude larger than the signal of the FFB object(s). One arrangement of device 10 is to configure applied field coils 18 so that the applied field is nearly canceled out in regions within the device, within which magnetic sensors 24 are positioned and attached (FIG. 1). Applied field coil element 12 is laid out on the surfaces of two printed circuit boards (PCBs) 14, 16. The two PCBs are placed parallel to each other, with the magnetic sensors placed between the boards. Each PCB 14, 16 accommodates a multiplicity of parallel, evenly spaced current paths 19 traveling in one direction in the center region of the board, with return paths 20 along the outer edges of the board, approximating two spiral patterns. The spiral patterns on one PCB are connected in series so that, when a current is passed through them, the resulting electric current distribution approximates a uniform sheet of current flowing in the Y-direction as shown in FIG. 1, over a substantial region near the center of the board. This region of the board is roughly defined by the area between the markers A—A in the X-direction and between the markers B—B in the Y-direction. This current distribution produces a magnetic field that is nearly uniform over a region of space near the center of the board. The two boards 14, 16 of this design are placed parallel to each other, with this relationship being shown. The PCBs are separated by a distance S which is small compared with the length and width of the central region of uniform current. The two PCBs are mounted so that the current paths 19 on one board are oriented parallel to the corresponding current paths on the other board. The current paths on the two boards are then connected in series to AC signal generator 22, so that the current flows in the same direction on both boards, the Y-direction in the arrangement shown. Signal source 22 can be equipped with a control device, as is known in the art, to cause the field to be pulsed, to be time varying, or to have a waveform with multiple frequencies. These time variations in the applied field can assist in distinguishing the responsive field from the environmental background fields, by synchronization of the sensing circuitry with the power supply. In a region surrounding the centers of the two PCBs 14, 16, the magnetic field produced by this arrangement approximates that produced by a pair of parallel, uniform sheets of current flowing in the Y-direction. In the space between the centers of the two PCBs, the net magnetic field is nearly zero since the contributions from the two current sheets approximately cancel each other. There is a small residual magnetic field, since perfect field cancellation is prevented by the finite size of the regions of the current sheets and the presence of return paths along the outer edges of the PCBs. However, due to the symmetry of the current paths in the two PCBs, the magnetic field is substantially zero in the plane midway between two PCBs. Magnetic sensor(s) 24 are placed in a plane parallel to PCBs 14, 16, with the plane of the sensors being located at the midpoint MP between the PCBs, so that the sensors are nearly in a zero field state with respect to magnetic fields generated by applied field coils 18.

FIG. 2 shows another view of the field coils with magnetic sensor, which could be an MR sensor, placed in a low-field region sandwiched between parallel circuit boards 14 and 16 as shown in FIG. 1. The current paths are shown with lines and arrows. The central region of each circuit board contains a number of parallel, evenly spaced traces 19 which are connected in series and which carry identical applied field currents.

FIG. 3 shows where sensor 24 is placed with respect to applied field coil 18. The top coil has been removed to show sensor positioning. The arrow on sensor 24 indicates the direction of its field sensitivity. Two methods are used to null out the field at the sensor location. First, a set of shims is used to adjust the position of the sensor between the two current sheets. This adjustment is needed because the applied field, given the finite size of circuit boards 14, 16, is zero only on the plane of symmetry midway between the two current sheets. With this coarse adjustment, a reduced residual field occurs at the sensor to a value roughly 300 times smaller than the field at the outer surface of the coil set. A fine balance adjustment is made by placing small tabs of metal near the sensor. By using balance tabs of both steel and aluminum foil, the in-phase and the out-of-phase components are canceled out of the magnetic field with respect to the AC current supplied to the applied field coil. A reduced residual field to a level roughly 30,000 times smaller than the field at the outer surface of the coil set occurs when current is applied. Any noise due to the variations in the AC supply is less than $10^{-8}$ of the field applied to an examined sample, that is, the tissue.

In detector assembly 10, geometrical variations of applied field coils 18 and sensor(s) 24 are important effects that this field-nulling system cannot remove. Temperature variations may cause subtle distortions in the geometry of the applied-field coils, or in the position of the magnetic sensor within the coils. Such distortions can perturb the balance of the field-canceling system, producing noise in the magnetic measurements.

The detector assembly provided herein minimizes effects caused by geometric distortion of the detector assembly by modulating the distance between a tissue of interest and the instrument's detector assembly at up to several hertz, with displacement of the detector assembly up to six inches. The change in the magnetic signal at the modulation frequency is then measured. The invention departs from methods used with conventional SQUID devices by moving detector assembly 10 while the patient remains stationary. The instrument herein performs this function by mounting the detector assembly, which includes applied field coils 18 and sensor 24, on a nonmagnetic platform, and oscillating the detector assembly back and forth at several hertz using a motor to drive a mechanism for producing that oscillatory movement. This mechanism can be a cam driven, spring biased plate, where the cam member is belt driven by the motor, or a reciprocating rod where the detector assembly is mounted to a plate that oscillates by a linear drive member, among others. Other reciprocating motion-type devices can be used as well to provide proper oscillatory motion with displacements of up to and around six inches, at motion frequencies up to and around 10 hertz. The detector assembly is mounted in a housing that provides support and positioning for the instrument. The housing and the components of the oscillatory motion mechanism are made of nonmetallic, nonmagnetic materials. Signal analysis described below extracts information from the signal output from magnetic sensor 24 that preferably determines iron concentration in a patient's liver.

The ability to move detector assembly 10 instead of the patient is significant since the overall instrument is much simpler and less expensive. Moving a SQUID type magnetic sensor is not permitted since any magnetic gradients in the environment produce signals that interfere with the direct current magnetic response measurements. These ambient magnetic gradients do not present problems in the measurements of this invention since AC applied fields are used. In addition, the room temperature sensor(s) 24 have much more tolerance compared to SQUIDs when being moved in the presence of the earth's magnetic field.

Another feature of the invention is the ability to measure weak variations of the magnetic field response of tissue, preferably the liver. For optimizing signal response when observing the liver response with respect to the noise of the magnetic sensor, it is necessary that the applied field penetrate more deeply into the body than is possible with applied field coils 18 in detector assembly 10. Also it is desirable to maximize the magnetic response from the liver with respect to the magnetic response from the overlying abdominal tissue and from the nearby lung. Most body tissues have weak diamagnetic susceptibilities similar to that of water, roughly $-9.0 \times 10^{-6}$ in SI units. This diamagnetic response is actually 30 times greater than the $3.0 \times 10^{-7}$ SI units that corresponds to liver iron at concentrations of around 0.2 milligrams per milliliter. The applied field coil of the present application optimizes the liver response with respect to the sensor noise and with respect to the interfering signals from the abdomen and the lung.

Figure 4:
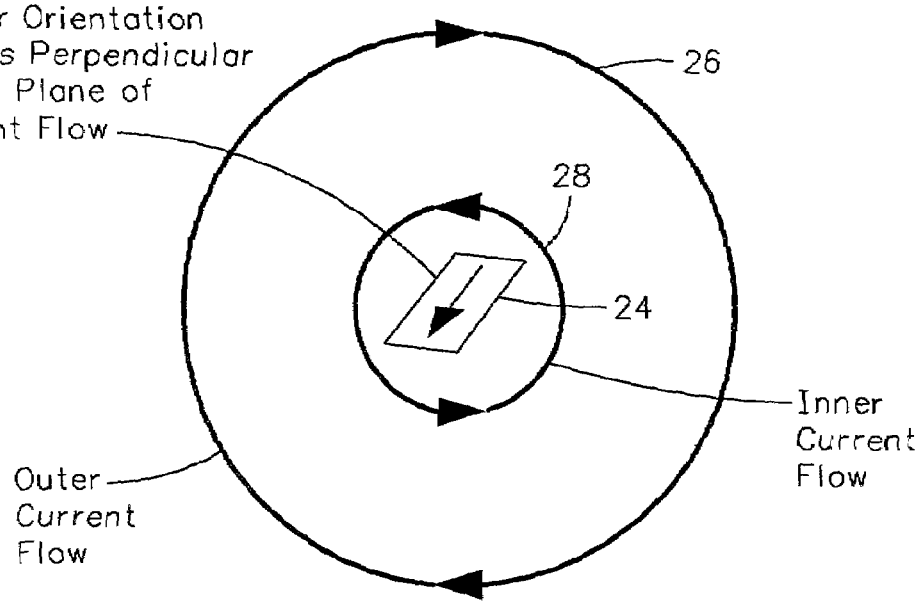
FIG. 4 is a schematic view of the applied field coil and sensor arrangement according to the invention.
Figure 5:
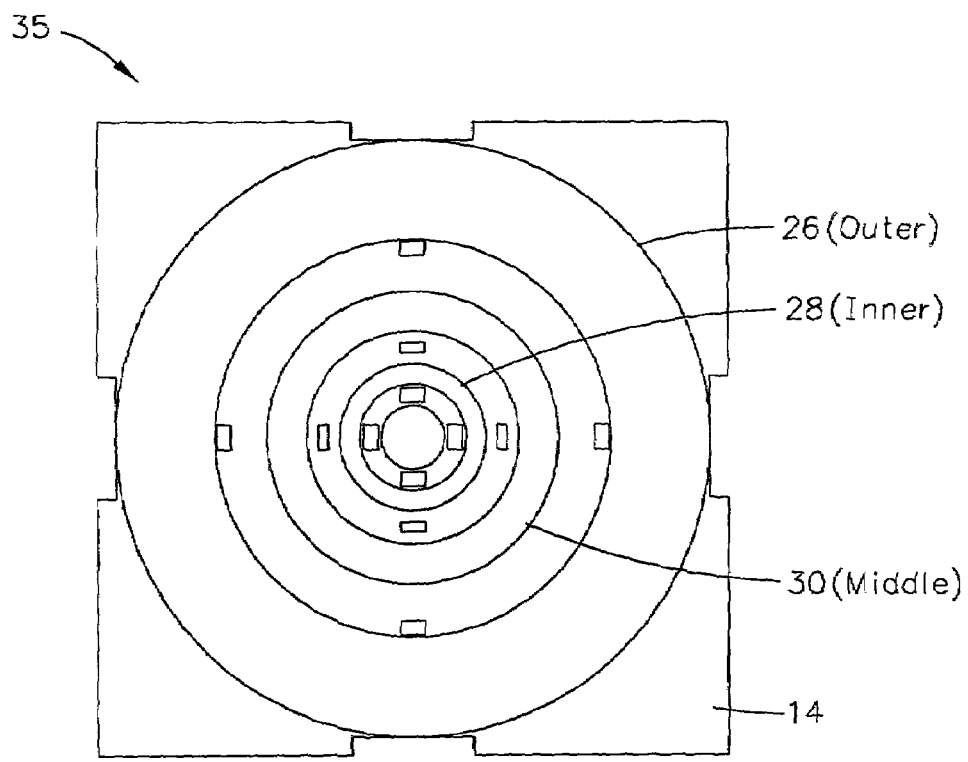
FIG. 5 is a plan view of an example of the actual coil geometry of the detector assembly of FIG. 4.

FIGS. 4 and 5 show the configuration according to one embodiment of the invention of an applied field coil arrangement 35 with a geometrical design that optimizes a response signal from the liver. Such a design adjusts the diameter of the applied field coil 26 to control how deeply the applied AC magnetic field penetrates into the patient's body. A circular coil of radius "a," for example, produces a field that falls off rather slowly out to distances comparable to "a," and then decays as $1/r^3$ at longer distances. Main field coil 26 allows for measurement of the liver response and evaluation of the response due to the susceptibility of the overlying abdominal tissues. Middle coil 30 may be optionally used in order to measure the signal from the overlaying abdominal tissue, since the AC field from coil 30 will not penetrate as deeply as the field from coil 26.

FIG. 5 shows the applied field coil arrangement of one embodiment of the detector assembly as it would exist on the PCB. The detector assembly comprises either two concentric circular spiral coils 26 and 28, or three concentric circular spiral coils 26, 28 and 30, but can include additional coils for designs that encompass the concept of the present invention. FIG. 5 shows the first coil 26, with a relatively large diameter, which produces a field that reaches deep into a patient's body. The resulting magnetic susceptibility response contains contributions from both the liver iron and the abdominal tissues. The diameter of coil 26 maximizes the liver iron contribution and minimizes the abdominal tissue contribution, so that variations in the susceptibility of the abdominal tissue have as little effect as possible on the measurement of liver susceptibility. A mean diameter in a range of around 15–50 cm for outer coil 26 has been found to be effective for proper liver iron measurements of a patient. However, subsequent work indicates that a somewhat smaller coil diameter, in the range of 5 to 15 cm, is preferred, in order to reduce the volume of tissue contributing to the susceptibility measurement and thus reduce possible errors due to the magnetic susceptibility response of the lung.

During magnetic susceptibility measurements small, innermost applied field coil 28 is connected in series with outer coil 26 in such a way that the current in inner coil 28 is in the opposite direction from that in the outer coil. The diameters and numbers of turns in the two coils are adjusted so that the magnetic field due to the inner coil cancels the magnetic field due to the outer coil in a region near the common center of the two coils, producing a small zone of substantially zero magnetic field. The magnetic sensor (24 in FIG. 4) is then placed in this zone of substantially zero magnetic field so that, as discussed above, fluctuations of the current in the applied field coils produce very little noise in the magnetic susceptibility measurements. The inner coil typically has a mean diameter of about 1.5 to 8 cm. Since the magnetic field due to the small, innermost coil 28 dies away rapidly with distance, the magnetic field in the patient's body tissues is produced almost entirely by outer coil 26.

FIG. 5 also shows intermediate-diameter coil 30, which can optionally be used in place of the outer coil 26 to produce a magnetic field that reaches a relatively short distance into the patient's body. Magnetic susceptibility measurements made using intermediate-diameter coil 30 will produce a magnetic susceptibility response whose main contribution comes from the patient's abdominal tissues. The results of these measurements can be used to evaluate the magnetic susceptibility of the abdominal tissues. This information can then be combined with the results of magnetic susceptibility measurements made using outer coil 26 to evaluate the magnetic susceptibility of the liver, while removing errors due to the susceptibility of the abdominal tissues. However, in another embodiment as discussed later herein, a water-bag is used instead of coil 30 to reduce errors in the liver susceptibility measurement due to the response from the abdominal tissue.

In magnetic susceptibility measurements made using intermediate-diameter coil 30, this coil is connected in series with small, inner coil 28 in such a way that the magnetic field is canceled at the location of the magnetic sensor.

Exemplary relative dimensions of the three concentric coils that make up the applied field coil are shown in FIG. 5. Each coil consists of one or more concentric loops. The number of loops in each coil is proportional to its diameter. This ensures that if any two coils are energized with equal but opposite current, the field at the center will be zero. This equal and opposite current is realized by making the appropriate electrical interconnections between the inner and outer coils and applying current to the two coils using the same current source. In a preferred embodiment, there are only two concentric coils 26 and 28, and outer coil 26 has about two times the diameter of coil 28 and about two times as many turns. In order to achieve the desired zero field in the center, minor adjustments can be made in various physical aspects of the coil arrangement to account for expected tolerances.

Applied field coils 26, 28, 30 can comprise traces on a printed circuit board. To generate the maximum field for a given current magnitude, similar coil sets can be positioned on both sides of circuit board 14, thus doubling the number of turns of each coil. In addition, stacks of circuit boards 14 can provide a sufficiently strong field to the examined tissue sample without the excessive ohmic heating (and the resulting undesirable thermal drifts) that can occur if too large a current is passed through a single circuit board. Alternatively, the printed circuit board can be replaced by wires, metal rods, or other electrical conductors supported by a rigid support structure that maintains the appropriate spatial relationship of the current carrying elements.

PCB 14 can be formed with a suitable number of holes for bolting individual boards rigidly to a solid G-10 fiberglass plate for structural stability, for example. Larger noncircular holes could be used to facilitate electrical connections between coils 26, 28, 30 on the stacked circuit boards. A hole at the center of the coil set allows for placement of a sensor 24 in a low field region close to the sample. A magnetic sensor is placed in the appropriate orientation so as to sense magnetic fields normal to the plane of the applied field coils (as indicated by FIG. 4). In this zero-field region, the sensor is practically immune to the applied field directly and only senses the body's response to the applied field.

As an example of the FIG. 5 configuration, outer coil 26 could consist of eight equally spaced concentric loops with a mean diameter of about 10 cm. Inner coil 28 would then have four equally spaced concentric loops with a mean diameter of about 5 cm. This applied field coil design ensures that when any pair of coils is energized with equal and opposite current the applied field at the center of the coils is zero.

Figure 15:
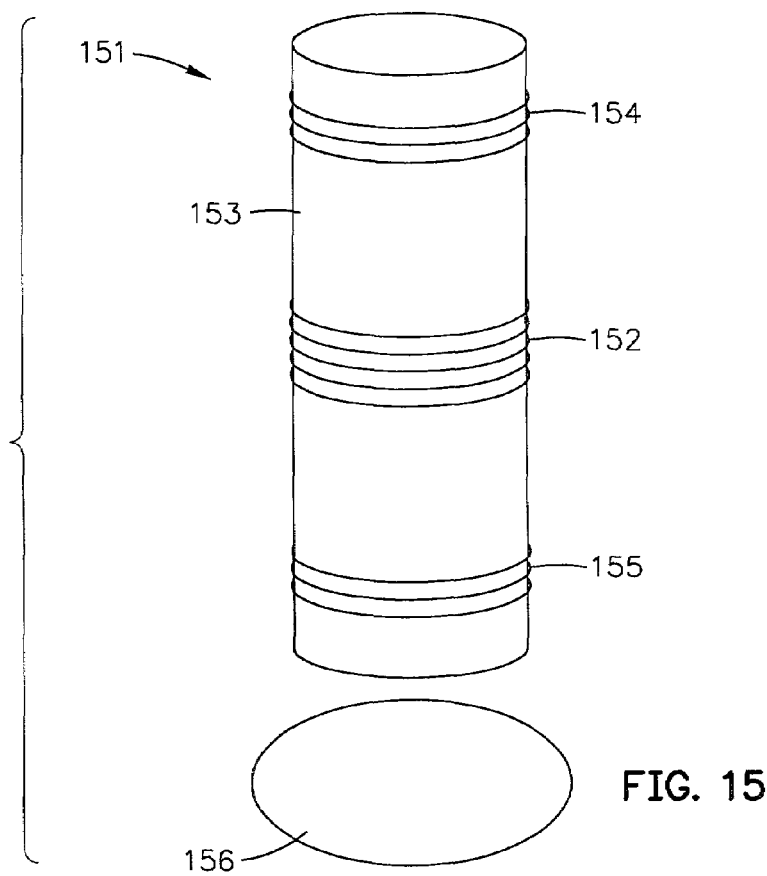
FIG. 15 shows a coil form sensor of the invention in relation to a tissue sample.

In an alternative embodiment shown in FIG. 15, sensor unit 151 includes applied field coil 152 consisting of a coil wound on a coilform 153 made of a non-magnetic and non-metallic material (such as fiberglass). The sensor comprises two equal and oppositely wound coils 154 and 155 which are configured symmetrically about applied field coil 152, both physically and electrically. This arrangement of the sensor coils constitutes a first-order gradiometer. Because of the symmetry of the sensor coils about applied field coil 152, they sense approximately the same amount of magnetic field. Moreover, because the two sensor coils are equally and oppositely wound, the induced voltage in each of them due to an AC magnetic field from the applied field coil is equal but opposite in sign. Hence the net voltage across both the sensor coils is substantially zero or close to zero. Hence the sensor coils are insensitive to the field applied by the applied field coil.

In order to measure the magnetic response from a sample, the sensor unit can be positioned with respect to sample 156 as shown in FIG. 15. This results in sensor coil 155 being closer to the sample compared to sensor coil 154. Hence the magnetic response of the sample is sensed at sensor coil 155 more strongly than that at coil 154. Correspondingly, the voltage induced at coil 155 is larger than that induced at coil 154. This results in a net voltage induced across the sensor coils. Therefore the gradiometer arrangement of the sensor coils allows for rejection of the response due to the applied field coil while at the same time being sensitive to the magnetic response from the sample. A similar result will be obtained by placing the sample close to coil 154 instead of coil 155.

Those skilled in this art will realize that there are other gradiometer configurations with more than two sensor coils which also provide for the rejection of the applied field while at the same time being sensitive to the signal from the sample. An example of such alternative configurations would use an applied-field coil wound as a first-order gradiometer, and a detection coil wound as a second-order gradiometer. In such a design, the detection coil would comprise two coils with equal areas and numbers of turns, wound in the same direction and placed at each end of the coil form, in series with a second coil, midway between the first two, which is wound in the opposite direction and has twice the number of turns as the first two coils. The applied-field coil would comprise two oppositely wound loops of equal area and having equal numbers of turns, placed at equal distances from the center coil of the second-order gradiometer.

Figure 8:
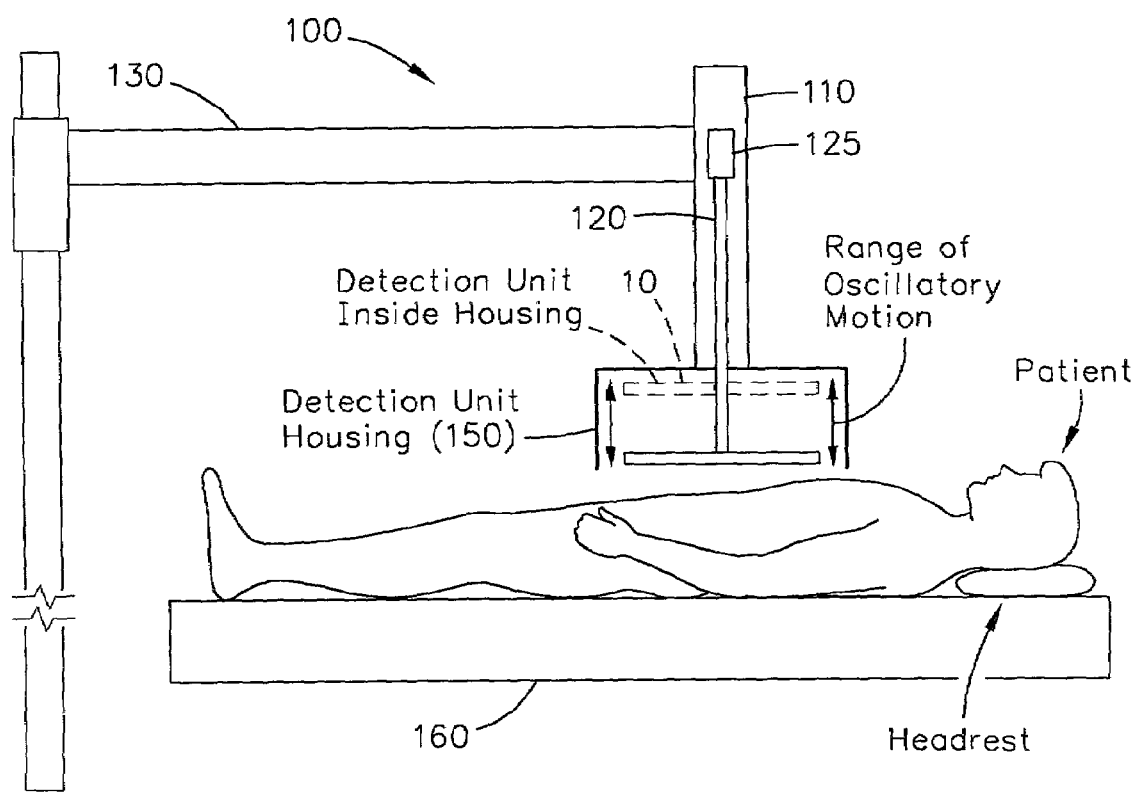
FIG. 8 shows an exemplary perspective view of the probing instrument of the invention in relation to a patient being examined.
Figure 16:
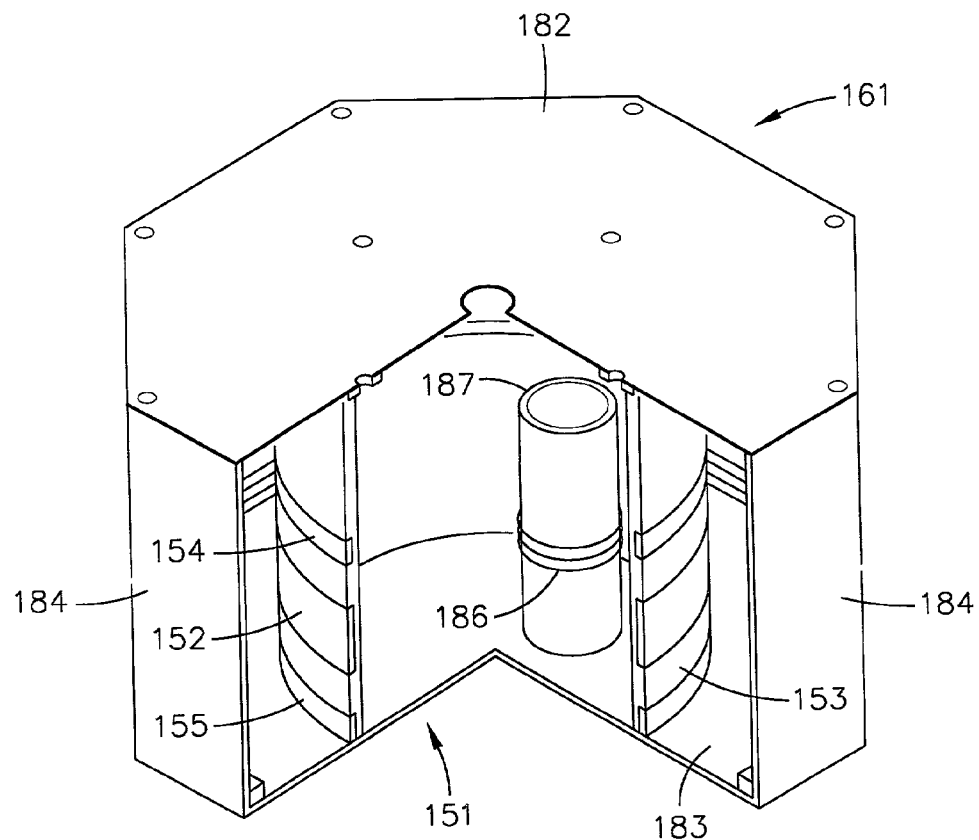
FIG. 16 is a partially cut away perspective view of an electrostatic enclosure housing the coil of FIG. 15 and showing a balance coil.
Figure 17:
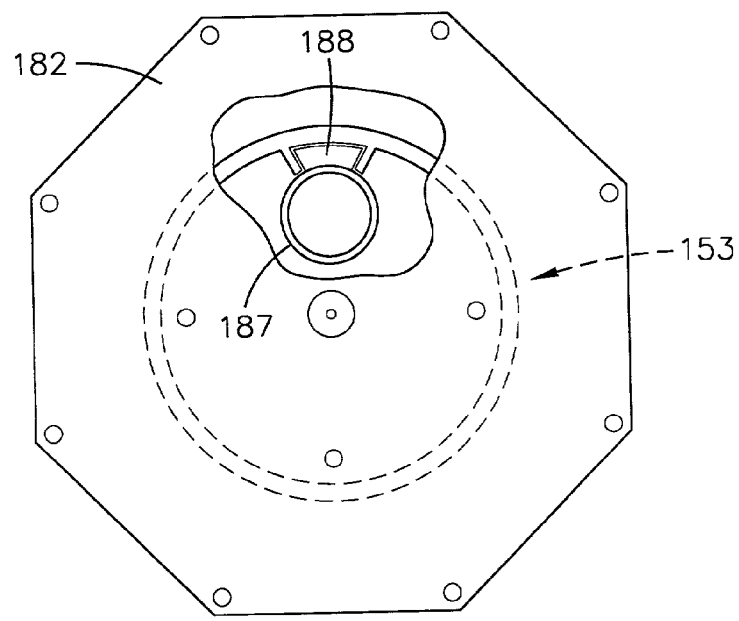
FIG. 17 is a top view of the housing of FIG. 16.

In order to achieve the necessary sensitivity to accurately measure the iron content in the liver, sensor unit 151 needs to be reciprocated with respect to the sample, like the sensor unit depicted in the embodiment of FIG. 8. Note also, that sensor 151 of FIG. 15 could be used in place of sensor 24 in the schematic depiction of FIG. 4. This reciprocating action allows for the mitigation or elimination of noise due to thermal effects. Also, sensor unit 151 can be more prone to electrostatic noise (due to electrostatic coupling between the sensor and the sample) than sensor unit 14 of FIGS. 4 and 5. To reduce or eliminate this noise an electromagnetic shield is placed around the sensor unit. FIG. 16 shows the placement of octagonal electromagnetic shield 161 around sensor unit 151 and between the sensor unit and the sample to be measured. The sample is placed below the shield shown in FIG. 16. The electrostatic shield consists of conducting material laid out in the form of thin strips connected in a branching pattern, so as to avoid loops of conductors which will result in any significant electromagnetic shielding of the sample from sensor unit 151. A top view of the shield unit of FIG. 16 is shown in FIG. 17.

Figure 18:
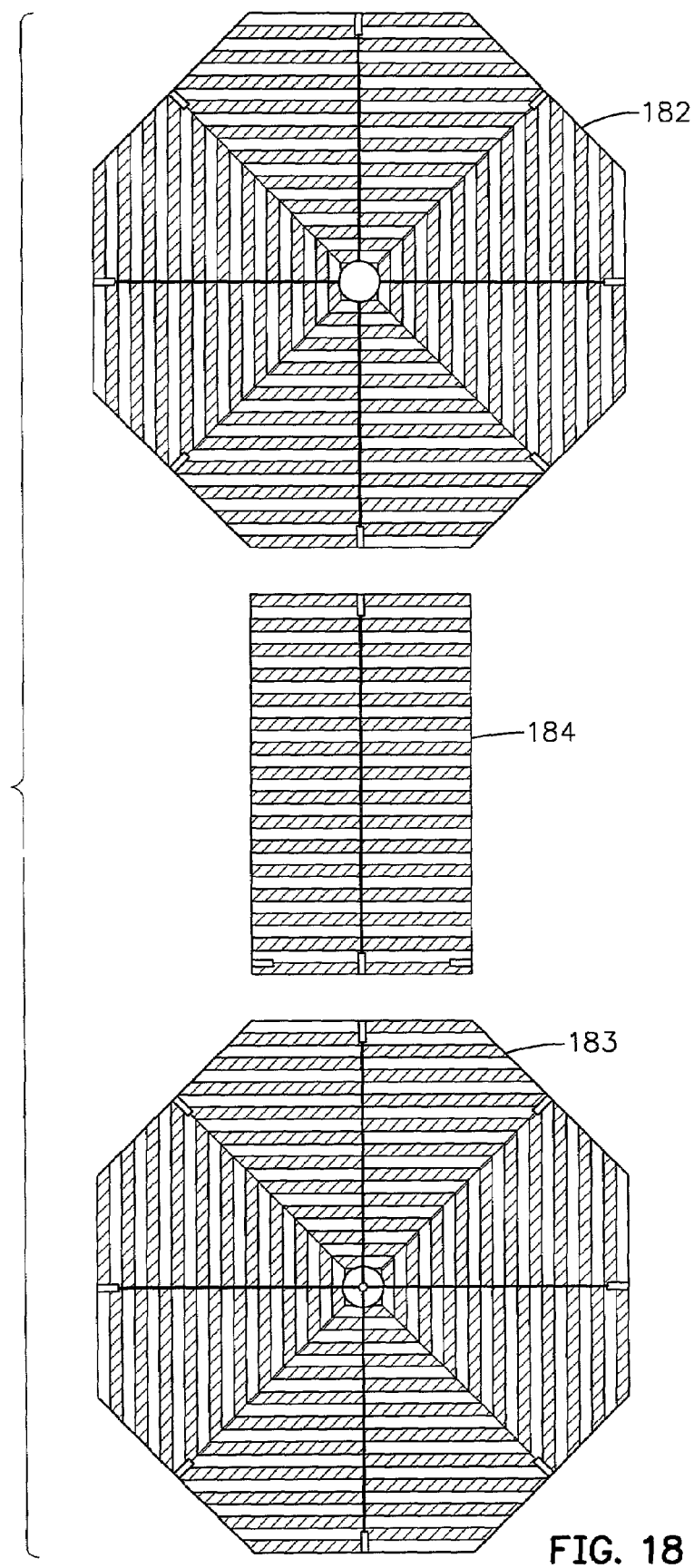
FIG. 18 shows in plan view some of the printed circuit boards from which the housing of FIG. 16 is formed.
Figure 19:
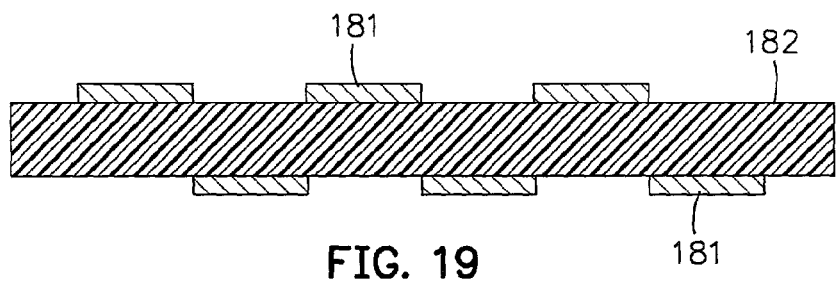
FIG. 19 is an enlarged, partial cross sectional view of a board from FIG. 18.

One possible configuration of an electrostatic shield is shown in spread out form in FIG. 18. Here, thin conducting strips 181 are laid out on the surface of a set of printed circuit boards (PCBs) 182, 183, 184 (see FIG. 19). The electrostatic shield consists of a octagonal box with eight side PCB panels 184 (only one is shown), and one top (182) and one bottom (183) PCB panel. Each PCB panel consists of closely spaced (0.25 mm), thin (0.25 mm) traces 181 of conductor covering the extent of the panel in a tree like arrangement, with branches radiating out but never forming a conducting loop. The thin conductor traces and the absence of conducting loops prevents the panel from acting as an electromagnetic shield due to induced eddy currents (which could attenuate or phase shift the AC magnetic fields used in the magnetic susceptibility measurements) while at the same time maximally covering each panel with conductive material to provide electrostatic shielding between the sample and the sensor coil. The ten PCB panels are suitably electrically connected to each other in order to provide a continuous electrostatic shield to the sensor unit while avoiding continuous loops of conductor that would produce electromagnetic shielding effects. Appropriate holes are provided in the electrostatic shield panels for leads to connect from the enclosed sensor unit to the appropriate electronics. While the use of the electrostatic shield is more beneficial for the gradiometer sensor coil design, it may also be used with suitable geometrical modifications for the PCB coil design of FIGS. 4 and 5.

An additional desirable feature of the design shown in FIG. 18 relates to the width of the conducting strips, and their placement on the two sides of the printed-circuit board. In order to minimize eddy-current effects, it is desirable to make the conducting strips as narrow as possible. However, limitations of PCB fabrication technology make it impractical to use strips narrower than approximately 0.01 inch, or separations less than about 0.01 inch between strips. When the electrostatic shield is laid out with the strips as narrow, and as closely spaced as is practical, the gaps between the conductive strips cover an area comparable to the strips themselves. In this case, in order to maximize the effectiveness of the electrical shielding, it is desirable to place strips on both sides of the PCB, in a staggered manner such that the strips on one side of the PCB cover the gaps between strips on the other side of the PCB. This is shown in the cross section of FIG. 19.

By way of example, the coil sensor of FIGS. 15 and 16 could be about 7 cm in diameter and have an axial length of about 5–15 cm. The enclosure of FIG. 16 would then have a diameter of about 8 cm and would have sufficient length to enclose the coil sensor.

While the applied field is mostly cancelled at the sensor coils due to their symmetric placement about the applied field coil, this cancellation is not usually complete since it is not possible to achieve perfect symmetry in the construction of the sensor coil. In view of this an additional "balance" coil 186 (FIGS. 16 and 17) is used to improve the cancellation of the applied field at the sensor. In one implementation shown in FIG. 16, balance coil 186 consists of 10–20 turns of insulated copper wire on a non-metallic, non-magnetic (for example, fiberglass) cylindrical coilform 187 about 1–1.5 inch in diameter. The balance coil is connected in series with the applied coil sensor and can be moved longitudinally (axially) so as to modify the coupling between it and one of the sense coils. This motion may be simply achieved by any suitable device. Coilform 187 may be mounted to a suitable bracket, shown as a wedge in FIG. 17, which may be movably mounted in a channel (shown V-shaped) arranged parallel to the longitudinal axis of coil sensor 151. This adjustable mounting structure is referred to by numeral 188. By modifying this coupling appropriately, one can achieve improved cancellation of the residual field which is in phase with the applied field at the sensor coils. The residual out-of-phase component is cancelled by placing appropriate conducting, but non-ferromagnetic, tabs (for example, copper) on the coilform. There are alternate methods other than the use of a movable balance coil to achieve improved cancellation of the applied field. One alternative method includes the use of ferromagnetic tabs (for example, steel or mu-metal) to improve the cancellation of any residual signal from the sensor coils in phase with the applied field. A third method would be to involve electronic sensing of the imbalance in the sensor coils and provide and use a feedback circuit to provide a compensating current at the appropriate phase to the applied field signal to a compensation coil in order to cancel out any in-phase or out-of-phase residual field at the sensor coils. These residual field cancellation methods can be used with either of the embodiments of the sensor unit described herein.

Figure 22:
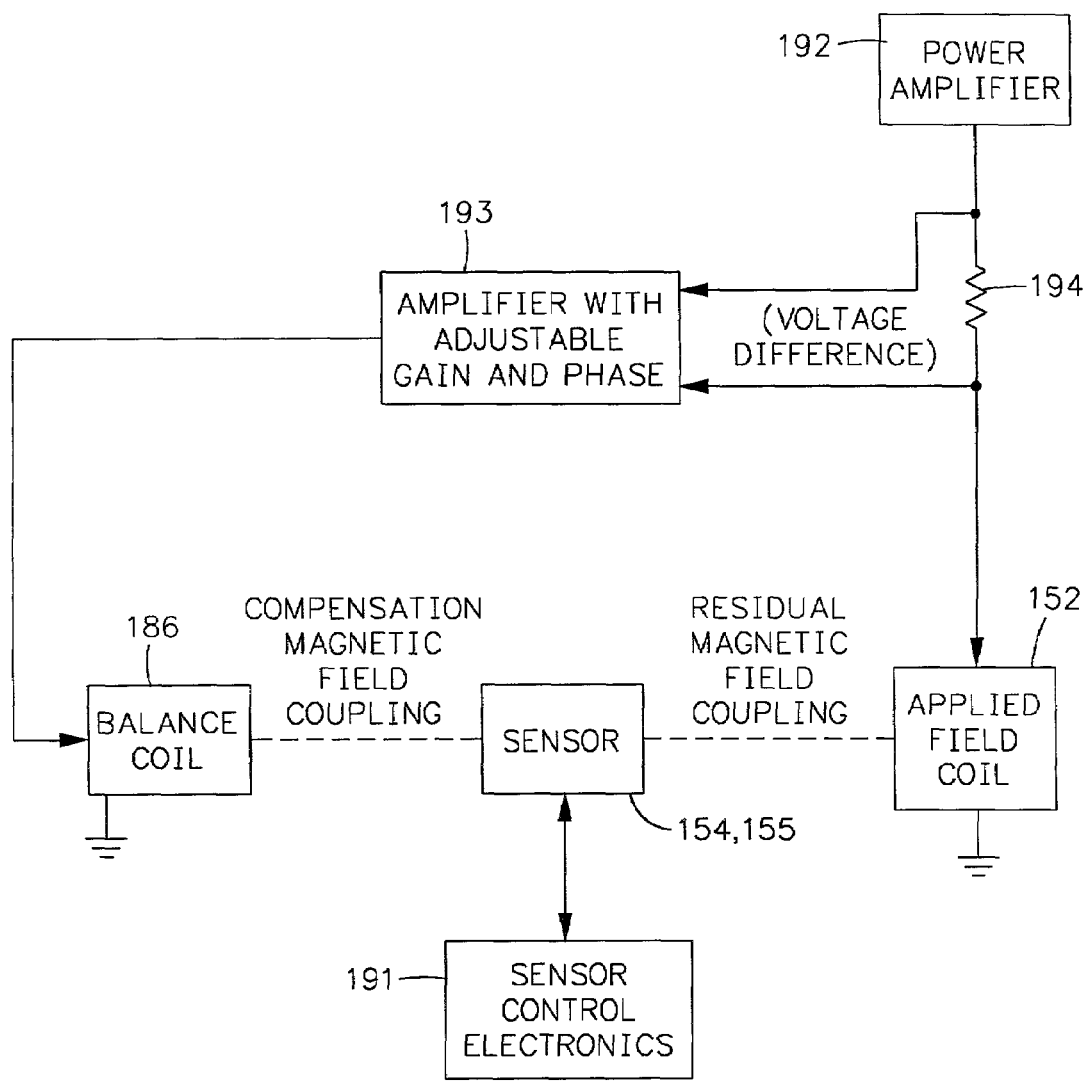
FIG. 22 is a block diagram of a simplified circuit incorporating the balance coil shown in FIG. 16.

A basic block diagram of a sensor system employing electronic field compensation with the balance coil of FIG. 16 is depicted on FIG. 22. With respect to the structure of FIG. 16, sensor coils 154, 155, applied field coil 152, and balance coil 186 are shown. For completeness of this exemplary circuit, power amplifier 192 is shown connected to amplifier 193 and monitoring resistor 194. The system is controlled by control 191. In this embodiment balance coil 186 need not be movable, and the residual field is cancelled by adjusting the gain and phase of amplifier 193.

In the past, measurements of liver iron concentration involving the cryogenically cooled SQUID systems typically used a "water bag" to help discriminate the signal from the liver from that of the overlying abdominal tissue. The magnetic susceptibility of the liver is only slightly different from that of the abdominal tissue (value close to that of water: $-9\times 10^{-6}$ SI units). The susceptibility contrast between the liver and the abdominal tissue is typically smaller than that between the air and the abdominal tissue. Hence the liver will appear as an anomaly in the body which is itself an anomaly in the surrounding air space. In biomagnetic susceptibility measurements, the susceptibility contrast between the abdominal tissue and the surrounding air produces a magnetic response which interferes with the measurement of the response due to the liver iron itself. In order to minimize this interfering signal, a bag filled with water is positioned to fill the space between the sensor and the surface of the patient's abdomen. The water, whose magnetic susceptibility is nearly the same as that of the abdominal tissue, essentially removes any magnetic susceptibility contrast at the outer surface of the abdomen, as if the entire magnetic measurement were being made in an environment filled with material of a constant magnetic susceptibility approximately equal to that of the abdominal tissue. The magnetic susceptibility measurement then responds primarily to the magnetic susceptibility contrast between the liver and the surrounding abdominal tissue. This magnetic susceptibility anomaly is due almost entirely to the iron in the liver.

The room temperature instrument can also be used with a water bag, to remove the interfering signal from the abdomen. Since reciprocation of the sensor coil toward and away from the sample or patient, as shown in FIG. 8, has been found to be a way to achieve the required sensitivity for accurate liver iron measurement, a water bag design which can be used with the sensor embodiments of this invention is configured to accommodate this reciprocating action. This will be discussed below in conjunction with the description of FIG. 10–14.

Figure 6:
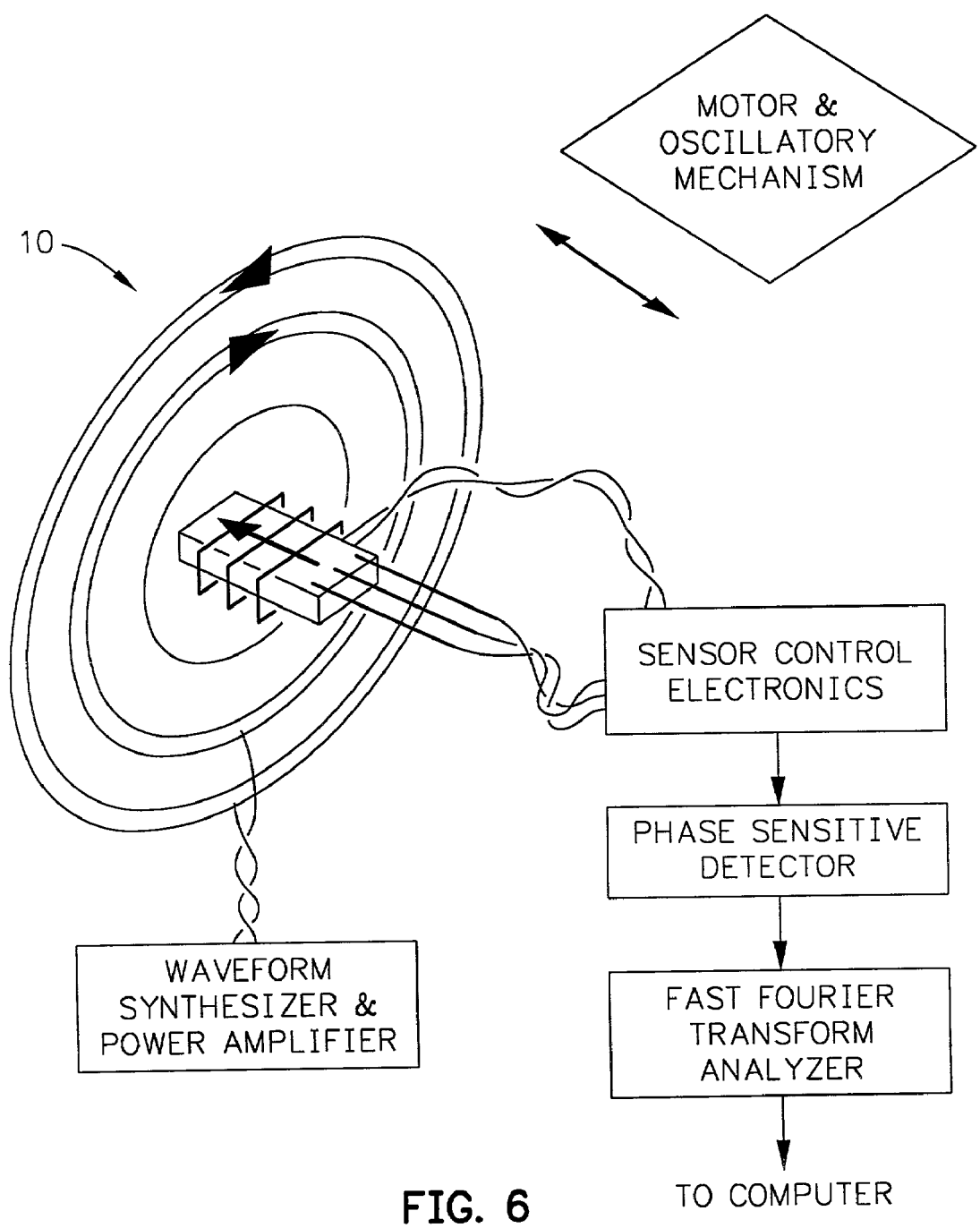
FIG. 6 is a block diagram of the interface assembly components incorporated with the coils of FIGS. 4 and 5.

Ancillary Hardware and Method of Use:

FIG. 6 shows detector assembly 10 and the interface assembly components attached thereto. Preferably, an induction coil sensor in one embodiment with the concentric loop coil 14 shown in FIG. 5, or the gradiometer coil sensor unit 151 shown in FIG. 15, can be used as the magnetic sensor.

A phase sensitive detector measures the component of the output of the magnetic sensor that oscillates in phase with the AC applied field. A Fourier transform analyzer calculates the component of the output of the phase-sensitive detector that oscillates in phase with the modulation of the sample-sensor distance. This provides a way to distinguish the signal of interest from the low-frequency noise caused by thermal drifts. The function of the phase sensitive detector can be performed by a lock-in amplifier, and the function of the Fourier transform analyzer can be performed by a spectrum analyzer. Preferably, either or both functions can be performed on a computer.

A signal source is used to generate an AC signal of between 25 Hz and 2 kHz. This signal, amplified by an audio frequency amplifier, provides a constant amplitude oscillating current through the applied field coils on the detection head assembly.

Figure 7:
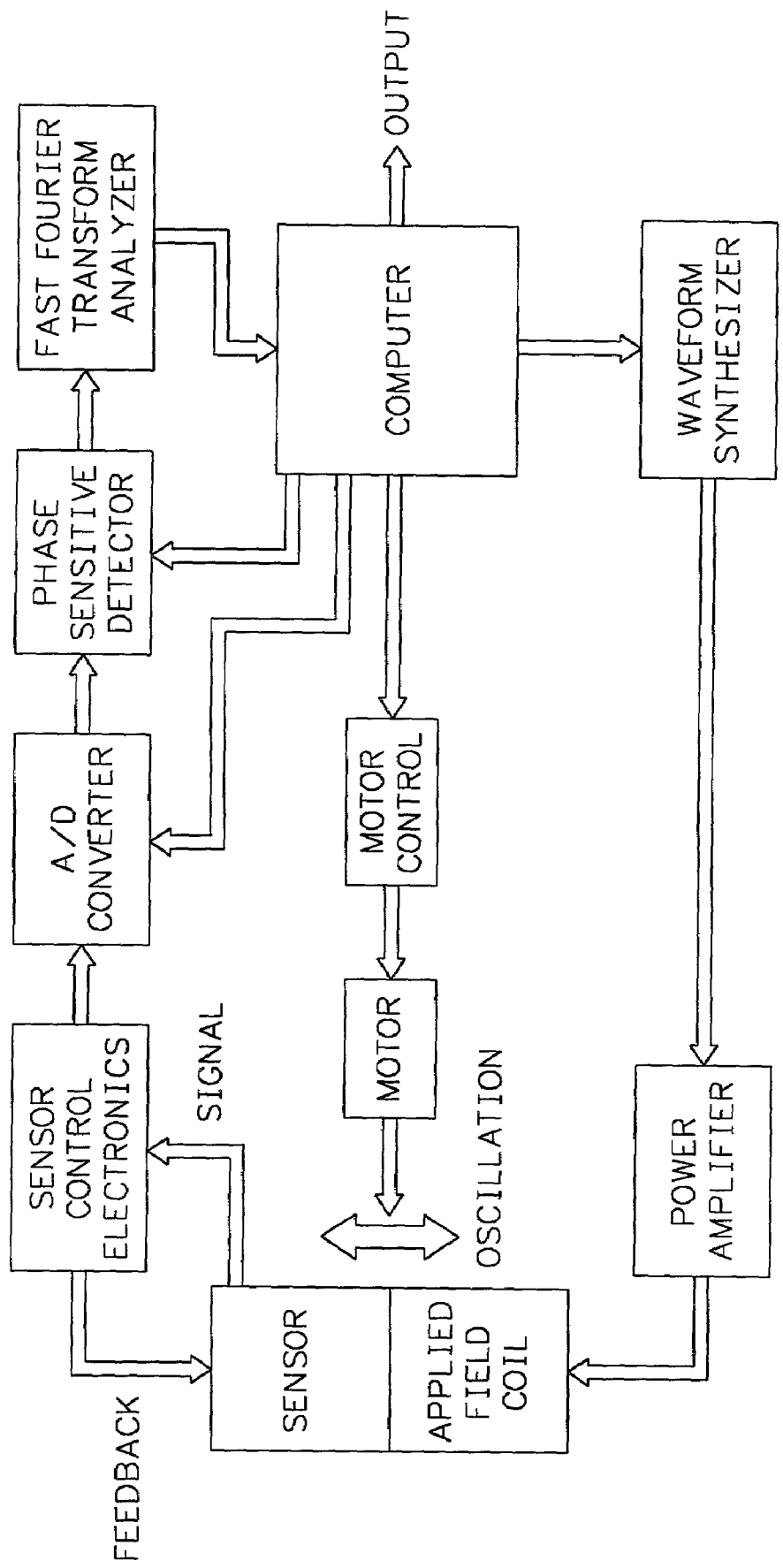
FIG. 7 is a block diagram with an applied field current source and analyzing components used in the probing instrument of the invention.

FIG. 7 shows the computer analyzer and control functions which process response signals from sensor 24, and output information regarding the concentration of paramagnetic materials in body organs. In the FIG. 7 embodiment the computer integrates and controls all instrument functions, including the modulation of the sensor-sample distance, the generation of the AC field coil current, and the processing of the magnetic sensor outputs to determine the magnetic susceptibility of the sample. The computer can be a personal computer with the required functioning signal cards and processors included. The motor indicated in FIG. 7 is preferably used to move the detector assembly toward and away from a patient's tissue area of interest. The fast Fourier transform analyzer is used to resolve the variation of the received signal which is synchronous with this motion. The waveform synthesizer is used to generate an AC signal, which is then amplified by the power amplifier to generate an AC current for the applied field coil. The waveform synthesizer function can be incorporated by the computer. The AC signal can have frequencies up to around 2,000 Hz, preferably avoiding harmonics of the power line frequency. The AC signal can be synchronized with the power lines, at a frequency commensurate with the power line frequency, in order to minimize noise due to the power lines.

Actual output from the computer can be a data storage device, a video display of useful medical information, or a connection to a computer system network.

A single medical instrument unit as shown in exemplary form in FIG. 8 as unit 100 incorporates the magnetic sensor control electronics, a motor/crank rod arrangement, as an example, for oscillatory movement of the distal end detector assembly, the waveform synthesizer and power amplifier, a lock-in amplifier, and a spectrum analyzer or equivalent computer device for signal analysis. Probe instrument 100 is shown with elongated positioning arm 130 wherein detector assembly 10 is mounted at distal end 110 of the arm. The distal end has motor 125 mounted within it, with the required oscillatory drive members 120 that move detector assembly 10 toward and away from the patient.

The patient is shown on a non-metallic table. Detector assembly 10 is positioned over the tissue area of interest, such as the patient's abdomen region where the liver is located. The detector assembly has the sensor mounted to reciprocating member 120 located within arm 110 that moves detector assembly 10 translationally toward and away from the distal end of the head member, the motion preferably being between one and six inches. The reciprocating action rate typically is in a range between around 0.5 to 10 hertz, such that modulation of detector assembly 10 filters out signal noise caused by temperature drifts in the applied field coils.

Reciprocating member 120 within the arm of probe instrument 100 allows modulation of the distance between the examined tissue and detector assembly 10, as explained above. The reciprocating member is made of nonmagnetic materials. In use, a water bag, further detailed in FIGS. 10–14, may be placed between detector assembly 10 and the patient for the purposes previously described.

Analysis is performed on the signal detected by the sensor to provide output information corresponding to the magnetic susceptibility of the liver. The concentration of iron in the liver can then be calculated from well established studies that directly relate liver iron susceptibility with liver iron concentration. The output of the instrument, in the form of liver iron concentration, can be displayed in ranges that extend from as low as about 30 micrograms per milliliter and to as high as the highest concentration found in patients with severe iron overload.

Variations to the apparatus of FIGS. 1–8 may include one or more of those discussed below. Modulation of the distance between the sample and the detector assembly can improve the signal-to-noise ratio of magnetic susceptibility measurements on any type of sample (that is, including samples other than the human body).

Variations to the invention include the methods and apparatus wherein modulation of the sample-sensor distance improves the signal-to-noise ratio of magnetic susceptibility measurements for the detection of ferromagnetic foreign bodies (FFBs) within the eye, brain, or body of a patient.

The instant invention describes an applied-field coil configuration, as shown in FIG. 5, consisting of two concentric circular loops carrying currents in opposite directions, in which the diameters and number of turns in the two loops are adjusted so as to cancel the magnetic field at the common center of the two coils. This applied-field coil design may be used in other types of magnetic susceptibility measurements. Similarly the applied-field coil and gradiometer sensor coil design shown in FIG. 15 may be used in combination with electrostatic shielding in other types of magnetic susceptibility measurements.

In particular, the concentric-loop coil design (FIG. 5) may be used with the apparatus and methods described in U.S. Pat. No. 5,842,986 for the detection of FFBs within the eye, brain, or body of a patient. The use of the concentric-loop coil would increase the magnetic susceptibility response of FFBs located deep below the surface of the patient's face, head, or body.

Measurement of appropriate magnetic-field gradients, or alternatively, the mapping of the magnetic-susceptibility response as a function of position, in order to compute the location of the FFB within the host, may be employed for the detection of FFBs in the eye, brain or body. This spatial mapping or magnetic gradient measurement may be achieved either by using an array of more than one magnetic sensor, or by using a single magnetic sensor and moving the detection unit (applied field coils and magnetic sensor). Either approach may be used in conjunction with the concentric-loop applied field coil configuration shown in FIG. 5.

The applied-field coil design of FIG. 5 may be modified to accommodate an array of more than one magnetic sensor. To reduce the noise produced by variations in the applied magnetic field, it is desirable to ensure that the field is as small as possible at the location of each magnetic sensor. The concentric-loop coil described above cancels the magnetic field at a single point, the common center of the concentric loops. If the radius of the inner coil is decreased slightly in relation to that of the outer coil, or if the current in the inner coil is increased slightly in relation to that of the outer coil, the magnetic field will be canceled not at a single point, but along a circle concentric with the two loops. Multiple sensors may then be placed at different locations on this circle, and the applied magnetic field will be canceled out at the location of each sensor. This arrangement makes possible the simultaneous measurement of the magnetic field response at multiple points in space.

As an alternative, the noise produced by applied-field variations may be minimized by measuring differences in the magnetic field between two or more magnetic sensors, as long as the magnetic sensors are positioned within the applied-field coils in such a way that the applied magnetic field is the same for each of the sensors. Such a result may be achieved with an applied field coil consisting of a circular loop, or multiple concentric loops, by placing each of the magnetic sensors at the same distance from the center of the loop(s).

Moreover, the applied field coils of the concentric coil design shown in FIGS. 4 and 5 can have differing dimensions and configurations to perform measurements at other tissue regions in the body. Also, switchable configurations of the applied field coil connections can be controlled by the computer, allowing for adaptive control of the instrument for multiple examining capabilities.

Figure 9A:
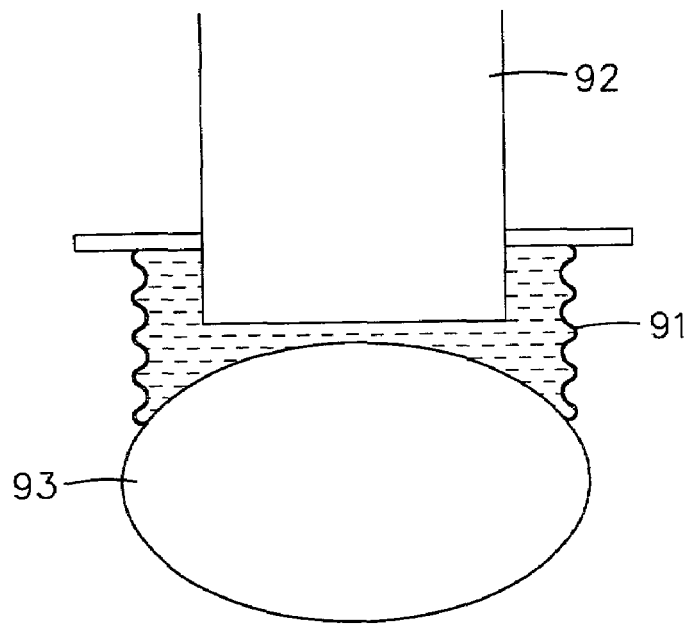
FIGS. 9A and 9B schematically show different positions of a prior art representation of a water-bag arrangement used with prior art magnetic susceptibility measuring devices.
Figure 9B:
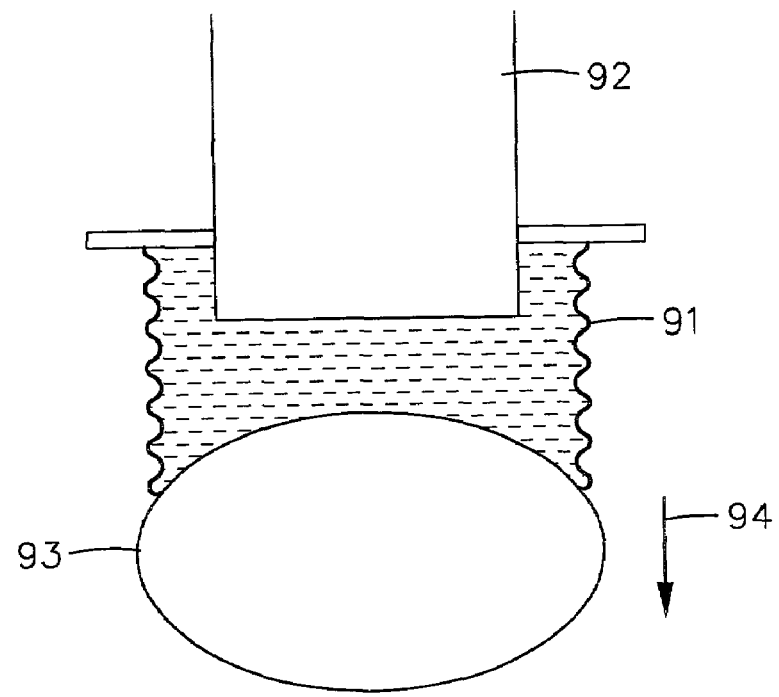

The prior art water-bag method to eliminate background tissue response was described in the background discussion and is shown in FIGS. 9A and 9B above. The present invention incorporates an improved water-bag method which increases the accuracy of the apparatus of FIGS. 1–8.

The present invention overcomes the disadvantages of the conventional water-bag technique.

Figure 10:
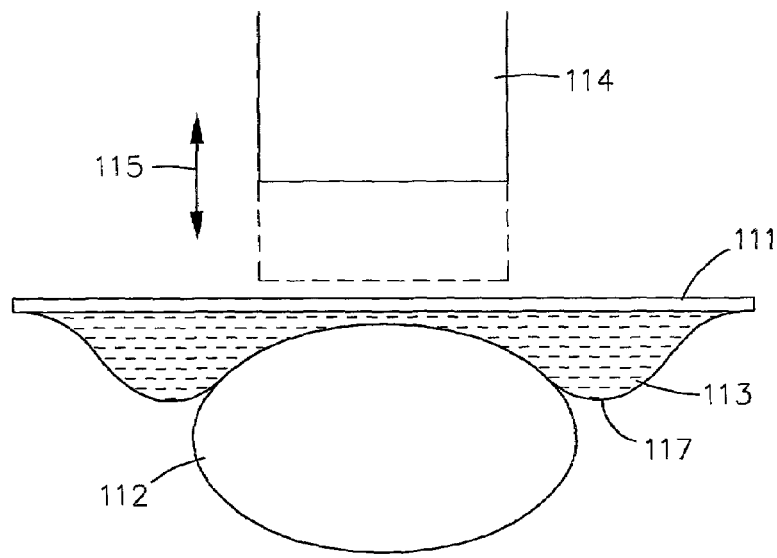
FIG. 10 is a schematic representation of the water-bag arrangement of the invention.
Figure 11:
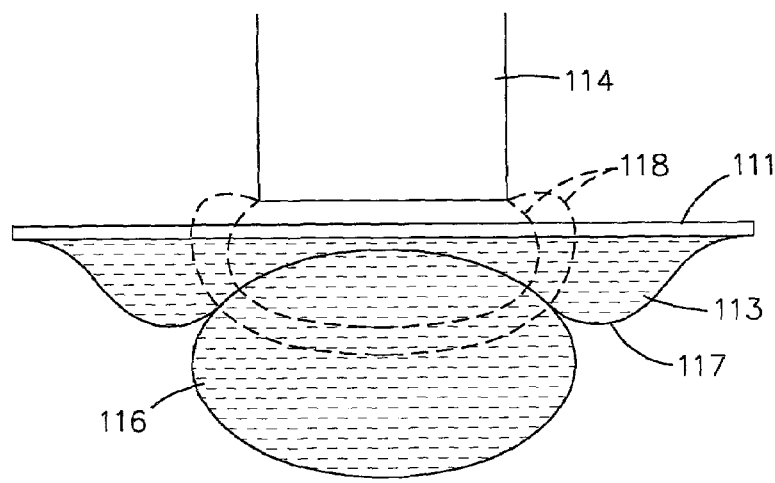
FIG. 11 shows how a reference signal may be developed for comparison when making measurements with the FIG. 10 embodiment.
Figure 21:
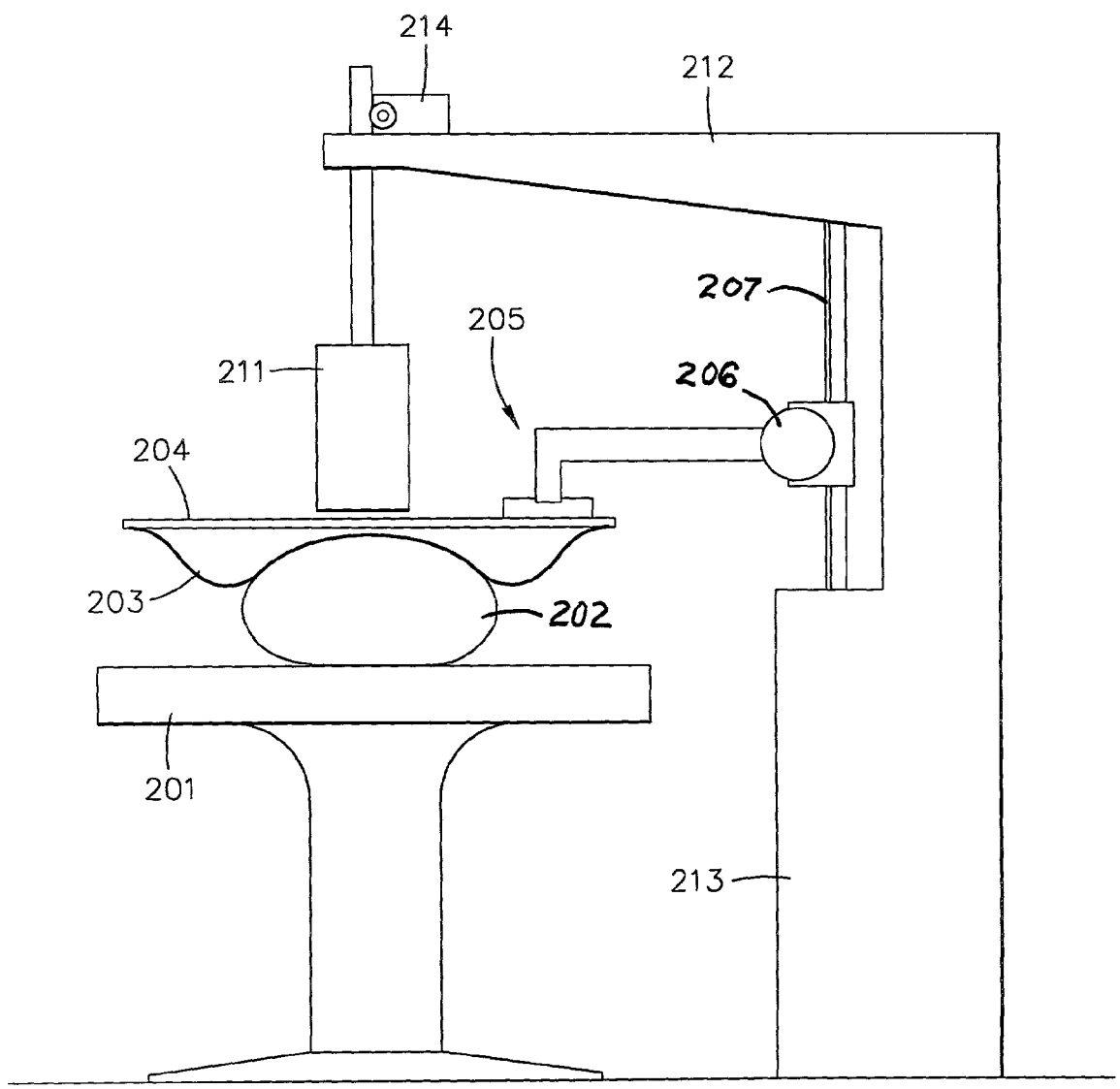
FIG. 21 is a schematic structure for pressing the water bag onto a patient.

With reference now to FIGS. 10 and 11, in this innovative technique the water bag does not expand and contract as the sample/sensor distance is changed. Instead, barrier plate 111 presses water bag 113 against the patient's abdomen to fill in any gaps between the barrier and the patient's body. This arrangement effectively replaces the air-tissue interface, the shape of which varies according to the outline of the patient's body, by an air-water interface which has a shape determined by the fixed barrier and is thus the same for every patient. An example of a structure for applying pressure to plate 111 and thereby pressing the water bag onto the patient to mold with the irregularities of the patient's body, is shown schematically in FIG. 21. Patient 202 is on table 201, with water bag 203 secured to plate 204 and pressed down by apparatus 205. Many possible mechanisms could be employed and as an example, motor 206 is shown movably coupled to a linear ratchet 207. Apparatus 205 is coupled between the motor and the plate. Sensor unit 211 is mounted for vertical motion, as previously described, to arm 212 of stable unit 213. Motive means for this purpose is represented by block 214.

To make a magnetic susceptibility measurement, sensor unit 114 (FIG. 10) is placed near the fixed barrier, on the opposite side of the barrier from the patient's body. The sensor unit is moved periodically toward and away from the barrier, as indicated by arrow 115. The height adjustment of the plate and the reciprocating motion of the sensor should be linked together in such a way that the distance of closest approach between the reciprocating sensor and the water-bag plate remains constant, and that such closest approach be maintained substantially constant. This sensor motion provides a periodic variation in the output of the sensor unit, whose amplitude is proportional to the magnetic susceptibility response of the material behind the fixed barrier. This magnetic susceptibility signal has a contribution from the iron in the liver and a contribution from the water bag and body tissues. The strategy is to configure the water bag and the sensor unit so that the tissue/water-bag contribution is the same for all patients.

In this arrangement, the susceptometer effectively sees a certain volume of material, bounded by the fixed barrier. Within the region that contributes significantly to the magnetic susceptibility measurement, all of the space on the other side of the barrier is filled either with water, or with body tissue having a magnetic susceptibility close to that of water. The magnetic susceptibility response due to the water bag plus body tissues is thus approximately equivalent to that of a volume of water that occupies the same space as the water bag plus the patient's body. On the side adjacent to the sensor unit, this volume is bounded by fixed barrier 111. This surface is the same for all patients. On all other sides, this water-filled volume is bounded by free surfaces 117 of water bag 113 and the patient's body. These surfaces will, of course, vary according to the shape of the patient's body, and how the water bag is being squeezed between the barrier and the patient's body. However, this variation will not significantly affect the magnetic susceptibility measurement, as long as the sensor unit is designed so that almost all of the measured response comes from a region that lies well inside these free surfaces. To make sure that this is the case, a number of design parameters can be adjusted, including the diameter of the applied-field coils, the geometry and placement of the magnetic sensors, the width of the fixed barrier and the volume and area covered by the water bag. (See FIGS. 4–6, 8 and 10–14.) It is also important to ensure that the water bag is sufficiently pliable to conform to the patient's body surface so that there are no air gaps in the critical region closest to the magnetic sensors.

By suitably adjusting these design parameters, it can be ensured that the magnetic susceptibility response from the water bag and body tissues is approximately the same for all patients. This contribution can then be evaluated ahead of time, as shown in FIG. 11, by making magnetic susceptibility measurements using a suitable water-filled phantom 116 in place of the patient's body. (A simple cylindrical container with a radius of curvature reasonably close to that of a typical patient's abdomen is sufficient.) Contours of constant sensitivity are represented by dashed lines 118. Once this water/tissue reference signal or background correction has been determined, it can be subtracted from the response obtained from a given patient, as in FIG. 10. The remaining magnetic susceptibility signal will be mainly due to the iron in the liver in cases where iron in the liver is being tested for.

The water bag thus has a different function in the present invention than in prior art. In previous water-bag methods, the water bag expands as the patient is withdrawn from the sensing apparatus, so that the body is effectively replaced by an equivalent volume of water, effectively eliminating the signal due to the air-tissue interface. In the present invention, the function of the water bag is not to expand while the patient is withdrawn, but simply to replace the variable shape of the patient's body with a constant, standardized shape defined by the barrier. As a result, the signal due to the air-tissue interface is not eliminated, but replaced by a constant background signal that is the same for all patients.

Figure 12:
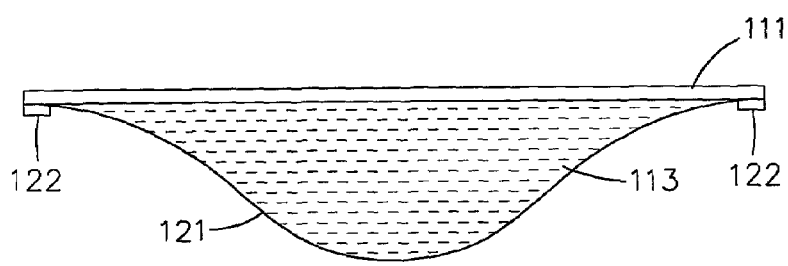
FIG. 12 is a side view separately showing the water-bag configuration of FIG. 10.

FIG. 12 shows one possible embodiment of the water bag. This design uses a thin elastic membrane 121 sealed at the edges 122 to generally rigid plate 111. The water is enclosed in the space 113 between the membrane and the plate. The membrane is configured to be thin enough to conform to any indentation in the patient's body, but thick enough to avoid leaks or tears and to keep the water bag from bulging too much under the weight of the water itself. It should be strong, pliant and somewhat stretchable in two dimensions. Latex rubber approximately 0.02" thick works well and other materials having the required characteristics could be used. The barrier plate itself is made of any suitable non-magnetic, non-conductive, substantially rigid material. Examples are transparent plastic and shatterproof glass. Visual transparency is preferred but is not necessary. It could be a relatively rigid plate that is machinable. Although the term "water bag" is used to refer to the pliable membrane attached to the plate to form a container, the liquid therein need not necessarily be water. It only needs to be a material such as a liquid or another deformable substance, such as a gel, having a magnetic susceptibility substantially equivalent to that of water, which matches that of human body tissue.

Figure 20:
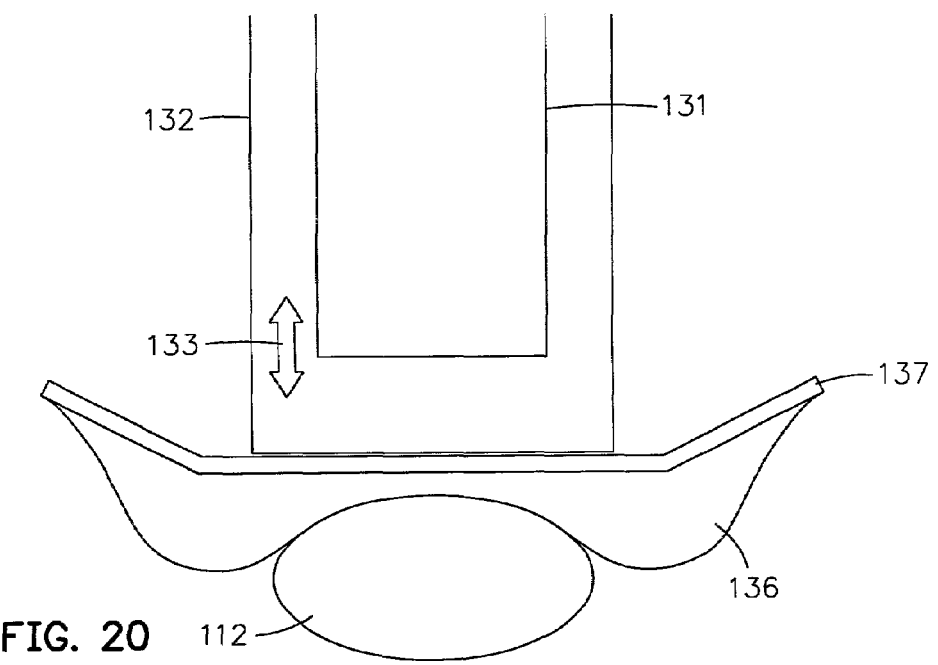
FIG. 20 shows a modified version of the plate of FIG. 10.

In the embodiment shown in FIG. 12, the fixed, substantially rigid barrier forming the top of the water bag is a flat plate. However, the fixed barrier may also have other shapes. One possible shape is shown in FIG. 20. Here, top plate 137 flares up at each end to provide room for the patient's shoulders and hips. Water bag 136 functions as previously described and the sensor apparatus may operate in accordance with the FIG. 10 embodiment or the FIG. 13 embodiment. Barrier plate 111, 137 could be formed with any suitable contours, as long as it and the water bag with which the plate functions provide the necessary effect. That effect is, as previously stated, to create an interface with the patient that the sensor perceives as being the same for all patents. It is only necessary that the plate be substantially rigid in that portion which must remain stable and non-deformed between the sensor and the patient, and that portion which is connected to a means for applying downward pressure to the plate. The plate or barrier is relatively thin so that the sensor can be brought as close as possible to the organ being tested. The liver, for example, is normally 15–20 mm below the abdominal skin surface. It is preferred that the top of the plate be 0.2–1.0 cm from the skin. The sensor, at its lowest point, will be preferably 0.5–3 mm above the plate, but it could be as much as 0.5 cm at its lowest point.

Figure 13A:
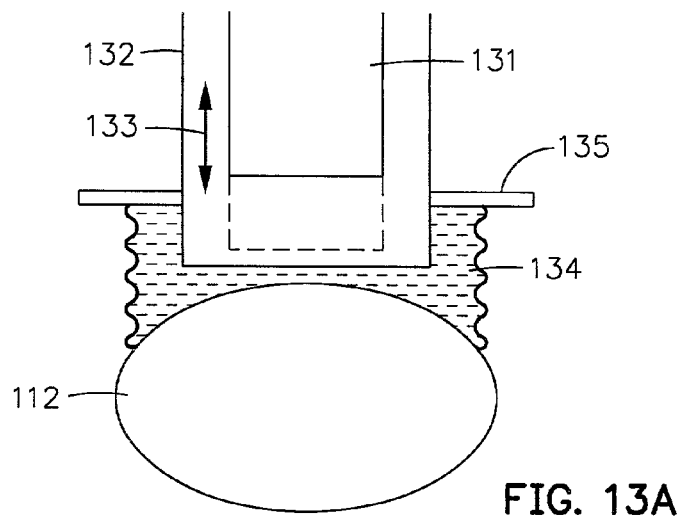
FIGS. 13A and 13B schematically show different positions of an alternative water-bag arrangement of the invention.

Yet another embodiment of the water bag is shown in FIG. 13A. Barrier 135 is set back from the patient's body by a suitable distance, which is preferrably in the range of 1–3 inches. The bottom surface of water bag 134 is formed by a thin, flexible elastic membrane such as a latex sheet. The sides of the water bag are defined by a flexible bellows, which presses down onto the surface of the patient's body. This embodiment, like previous water-bag designs, uses a bellows to define the sides of the water bag. However, in previous designs, the bellows expands as the patient is withdrawn from the susceptibility sensing instrument. In the present invention, however, the bellows serves only to match the rim of the water-filled enclosure to the irregular curved shape of the patient's body. The water bag then functions, as described above, to replace the variable shape of the patient's body with a standard shape.

Figure 13B:
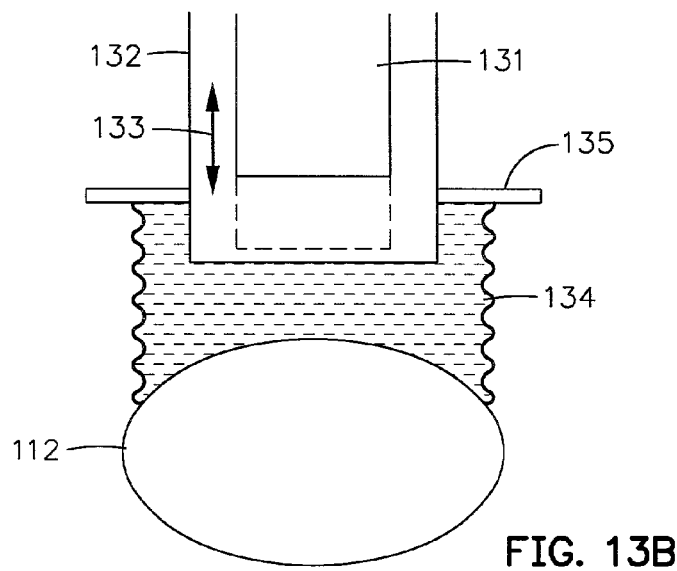

An alternative method of using a water bag is shown in FIGS. 13A and 13B. The method described above is useful when the output of the magnetic susceptibility measurement is sufficiently stable over time, so that the signal from a standard phantom can be measured, and then subtracted from the signal obtained from each patient. If there are drifts in the output of the sensor unit, these drifts must be slow enough to permit measurement of the standard phantom, set up and measure the patient, and then recheck the standard phantom. The method of moving the sensor unit periodically toward and away from the patient does a great deal to minimize drifts in the sensor output. However, even with this reciprocating-motion technique, there sometimes occurs a subtle, but persistent drift in the output of the magnetic susceptibility measurement over time. To combat this residual drift the reciprocating-motion technique is combined with an expanding-bellows water bag.

In FIGS. 13A and 13B, sensor unit 131 moves up and down (arrow 133) periodically inside enclosure 132. In this case, however, the entire measurement assembly, consisting of the sensor unit, the motion mechanism, plate 135 and fixed outer enclosure 132, is mounted on a slide mechanism, so that it can be moved up or down, toward or away from the patient 112. Filling the space between this enclosure and the patient is water bag 134 with an expandable-bellows, somewhat similar to those used in conventional biomagnetic susceptometers.

To determine the magnetic susceptibility response of the patient, the process starts with the bellows substantially collapsed (FIG. 13A), and the water in the water bag filling any gaps between the patient and the fixed enclosure. A magnetic susceptibility measurement is made as described earlier, moving the sensor unit periodically up and down within enclosure 132, and recording the periodic change in the amplitude of the AC magnetic field at the sensor. The entire measurement unit is then moved up away from the patient (FIG. 13B), adding water to the water bag so as to fill in the space between the patient and the outer enclosure of the sensing unit. Another magnetic susceptibility measurement is immediately made using the same reciprocating sensor motion technique, and the result of this second measurement is subtracted from that of the first measurement. This measurement sequence permits the drifts in the sensor output to be subtracted out more effectively, because it can be performed relatively rapidly, without having to move the patient between the two measurements.

In effect, this method is a double-modulation technique. The bulk of the drift is first removed by reciprocating the sensor unit at a frequency near 1 Hz, and monitoring the amplitude of the resulting periodic modulation of the sensor output. Any remaining drift is then removed by comparing two such measurements, one with the sensor assembly next to the patient and one with the sensor assembly moved away from the patient.

This double-modulation technique differs from the previous water-bag method in two key respects. First, it involves the simultaneous use of two types of motion, the reciprocating motion of the sensor unit at a frequency near 1 Hz, and the withdrawal of the entire sensing instrument from the patient over a period of several seconds. The combination of these two motions serves to remove thermal drifts and other slow drifts in the output of the sensing instrument. This reduction of drift effects is potentially important for the room-temperature biomagnetic susceptometer. Second, the double-modulation technique described above involves moving the sensor unit, instead of the patient. This improvement, which is possible because the magnetic susceptibility measurement is made using an oscillatory magnetic field, can potentially reduce costs, by eliminating the need to place the patient on a bed that moves up and down.

The discussion above focuses on the use of magnetic susceptibility measurements to determine concentrations of iron in the liver. However, this method can be used in any situation where magnetic susceptibility measurements are used to detect magnetic susceptibility anomalies within a host. Examples of other applications may include the use of susceptibility measurements to detect ferromagnetic foreign bodies in the eye and brain, as well as the use of magnetic tracers to study motility and transit times within the gastrointestinal system.

Figure 14:
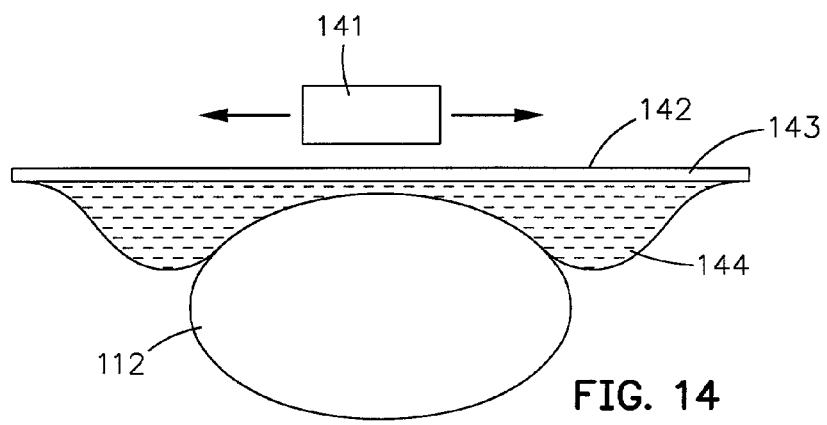
FIG. 14 is similar to FIG. 10, showing lateral motion of the sensor of the invention.

In the discussion above, the sensor unit is visualized as moving toward and away from the patient, in order to cancel out the effects of slow drifts in the sensor output. It is also possible, as shown in FIG. 14, to scan sensor unit 141 along surface 142 of the barrier 143, in order to map out the magnetic susceptibility response of the host. This technique is potentially useful, for example, in the detection of ferromagnetic foreign bodies. This scanning technique may also be useful in liver iron measurements, as a way of mapping out the susceptibility response of surrounding tissues, such as the lung. In this context, water bag 144 removes variations in the magnetic susceptibility response due to the irregular shape of the outer surface of the patient's body 112, permitting detection of localized peaks in the magnetic susceptibility response that indicate the presence of ferromagnetic foreign bodies below the surface.

Either the concentric coil design of FIGS. 4 and 5, the parallel-sheet coil design of FIGS. 1 and 2, or the gradiometer coil design of FIG. 15, may be used as sensor unit 141 to scan the surface of a sample as shown in FIG. 14 for magnetic anomalies that may indicate the presence of ferromagnetic foreign bodies.

The probe instrument of this invention allows for precision determination of concentration of paramagnetic materials in a body organ, in particular, the liver. The water-bag structure enables the instrument to provide rapid and accurate readings by quickly eliminating background tissue response. Several embodiments of the invention have been described above. It is likely that modifications and improvements will occur to those skilled in this technical field which are within the scope of the appended claims.

What is claimed is:

1. A method for noninvasive determination of magnetic susceptibility variation in a patient by measuring magnetic susceptibilities of selected tissue of the patient, the method comprising:
   providing an instrument which includes at least one magnetic sensor, an applied field coil and a current source connected to the applied field coil and means for processing sensed signals from the at least one magnetic sensor;
   positioning on the patient a flexible bag substantially filled with deformable material having a magnetic susceptibility substantially similar to that of body tissue, said bag being attached to a substantially rigid barrier, the barrier being spaced a predetermined distance from the patient by the material-filled bag, which predetermined distance remains substantially constant during a measuring sequence, the amount of deformable material in the flexible bag remaining constant during a measuring sequence, the instrument being moved with respect to the barrier during the measuring sequence;
   positioning the instrument external to the patient in proximity to the tissue of interest and adjacent the barrier;
   supplying the applied field coil with current thereby applying a magnetic field to the tissue of interest;
   sensing a response from the tissue of interest wit the instrument; and
   outputting data corresponding to the magnetic susceptibility variation in the tissue.

2. The method recited in claim 1, wherein an alternating current is supplied to the applied field coil.

3. The method recited in claim 1, wherein the method further comprises providing the instrument with displacement means for displacing the magnetic sensor and the applied field coil simultaneously thereby compensating for noise introduced to the sensed signals.

4. The method recited in claim 3, wherein the displacement means operates between about one to six inches.

5. The method recited in claim 3, wherein the displacement means operates between about 0.5 to 10.0 hertz.

6. The method recited in claim 1, wherein the outputting of data corresponding to the magnetic susceptibility variation in the human body comprises concentrations of paramagnetic material in the tissue of interest.

7. The method recited in claim 6, wherein the paramagnetic material is iron and the tissue of interest is a liver.

8. The method recited in claim 7, wherein the outputting of data corresponds to concentrations of iron in the liver and the resolution of the measurements corresponds to about 30 micrograms per milliliter.

9. The method recited in claim 1, wherein the positioning step functionally replaces the irregular or variable shape of the patient's body with a volume of material similar in magnetic susceptibility to body tissue, whose surface has a constant shape defined by the rigid barrier.

10. An apparatus for noninvasively measuring magnetic susceptibility variations in the body tissue of a patient to determine a compositional state in the body, the apparatus comprising:
    a detector assembly that includes:
       at least one magnetic sensor and an applied field coil for generating a magnetic field;
       a current signal generating source which connects to said applied field coil; and
       means for processing signals from said at least one magnetic sensor of observed magnetic susceptibility variations in body tissue;
    a non-conductive, non-magnetic, substantially rigid barrier;
    a flexible membrane sealed to said barrier to form a container therewith, there being a deformable material within and occupying most of the volume within said container, said material having a magnetic susceptibility substantially equivalent to that of the body tissue, said container being shaped and configured to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and
    means for outputting data from said detector assembly corresponding to a compositional state in the body tissue.

11. The apparatus recited in claim 10, wherein the current signal generating source provides alternating current (AC).

12. The apparatus recited in claim 10, wherein the means for processing signals from the at least one magnetic sensor comprises a processor for analyzing the signals obtained from the magnetic sensor.

13. The apparatus recited in claim 10, wherein the means for processing signals further comprises outputting means for displaying paramagnetic material concentration.

14. The apparatus recited in claim 13, wherein the paramagnetic material is iron.

15. The apparatus recited in claim 10, wherein to applied field coil is designed to create a first zone of a finite magnetic field within a selected region of the body, and a second zone of substantially zero magnetic field outside the selected region; and
    said at least one magnetic sensor is positioned within said second zone of substantially zero magnetic field.

16. The apparatus recited in claim 15, wherein said applied field coil comprises two parallel flat coils and a connecting circuit between said two parallel coils causing current to flow in identical directions at corresponding locations in said two flat coils, thereby simulating parallel uniform sheets of current.

17. The apparatus recited in claim 15, wherein said applied field coil comprises at least two concentric coils and a connecting circuit between said at least two concentric coils causing current to flow in opposite directions, thereby canceling the effects of a magnetic field caused by current flowing through said applied field coil at a central region of said at least two concentric coils.

18. The apparatus recited in claim 17, wherein the larger of said concentric coils has a diameter ranging between about 15 to about 50 centimeters.

19. The apparatus recited in claim 17, wherein there are at least three concentric coils, the outermost coils include at least two coils which are alternatively switched with the current source, whereby sufficient information can be derived independently as to the susceptibility of a deep lying tissue area in the body compared to a corresponding surface tissue area.

20. The apparatus recited in claim 19, wherein the deep lying tissue area is the liver and the overlying surface tissue area is abdominal tissue.

21. The apparatus recited in claim 15, wherein said detector assembly is multiple stacked applied field coils.

22. The apparatus recited in claim 10, wherein said at least one magnetic sensor attaches to a central region relative to the applied field coil.

23. The apparatus recited in claim 10, wherein said at least one magnetic sensor attaches to a central region relative to said applied field coil and said applied field coil is attached to a planar substrate.

24. The apparatus recited in claim 10 wherein said at least one magnetic sensor is a magnetoresistive sensor.

25. The apparatus recited in claim 24, wherein said at least one magnetoresistive sensor is part of a Wheatstone bridge sensing circuit.

26. The apparatus recited in claim 25, and further including magnetic sensor compensating electronics and a feedback coil disposed about said magnetoresistive sensor for locking an optimum operating point by applying a compensating electrical current from compensating electronics to said feedback coil thereby maintaining constant measurement sensitivity of the apparatus.

27. The apparatus recited in claim 10, wherein said at least one magnetic sensor is a fluxgate sensor.

28. The apparatus recited in claim 10, wherein said at least one magnetic sensor is a magnetoinductive sensor.

29. The apparatus recited in claim 10, wherein said detector assembly further comprises a means for oscillating said detector assembly.

30. The apparatus recited in claim 29, wherein said detector assembly is housed in a housing structure for positioning said detector assembly in proximity to a surface of the human body, and said means for oscillating said detector assembly comprises a motor with attached drive members tat move said detector assembly.

31. The apparatus recited in claim 10, wherein said detector assembly comprises an applied field coil on a cylindrical coilform and sensor coils axially spaced from said field coil on either side thereof.

32. The apparatus recited in claim 31, wherein said sensor coils are oppositely around in a gradiometer configuration.

33. The apparatus recited in claim 31, wherein said coilform is formed of non-magnetic, non-metallic material.

34. The apparatus recited in claim 10, wherein said deformable material is water.

35. The apparatus recited in claim 10, wherein said deformable material is a gel.

36. A magnetic susceptibility detector device comprising;
an applied field coil configured to connect to a current source, said field coil being configured to create a first zone of a finite magnetic field within a selected region of an observed specimen, and a second zone of substantially zero magnetic field outside said selected region, said applied field coil having at least two concentric electric current carrying coils of conductor material;
a sensing device comprising at least one magnetic sensor, said at least one sensor being positioned within said second zone of substantially zero magnetic field;
a non-conductive, non-magnetic, substantially rigid barrier; and
a flexible membrane sealed to said barrier to form a container therewith, there being a deformable material within and substantially filling said container, said material having a magnetic susceptibility substantially equivalent to that of the body tissue, said container being shaped and configured to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made.

37. The device recited in claim 36, wherein said at least one magnetic sensor is a magnetoresistive sensor.

38. The device recited in claim 36, wherein said at least one magnetic sensor is a fluxgate sensor.

39. The device recited in claim 36, wherein said at least one magnetic sensor is a magnetoinductive sensor.

40. The device recited in claim 36, wherein said sensing device comprises an applied field coil on a cylindrical coilform and sensor coils axially spaced from said field coil on either side thereof.

41. The apparatus recited in claim 40, wherein said sensor coils are oppositely around in a gradiometer configuration.

42. The apparatus recited in claim 40, wherein said coilform is formed of non-magnetic, non-metallic material.

43. The apparatus recited in claim 36, wherein said deformable material is water.

44. The apparatus recited in claim 36, wherein said deformable material is a gel.

45. An apparatus for noninvasively determining magnetic susceptibility variations in body tissue, the apparatus comprising:
a detector assembly comprising:
at least one magnetic sensor and an applied field coil for generating a magnetic field wherein the applied field coil is designed to create a first zone of a finite magnetic field within a selected region of the body, and a second zone of substantially zero magnetic field outside the selected region; and
said at least one magnetic sensor is positioned within said second zone of substantially zero magnetic field;
means for oscillating said detector assembly;
a current signal generating source which connects to the applied field coil;
a non-conductive, non-magnetic, substantially rigid barrier;
a flexible membrane sealed to said barrier to form a container therewith, there being a deformable material within and substantially filling said container, said material having a magnetic susceptibility substantially equivalent to that of the body tissue, said container being shaped and configured to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and
means for processing signals from said at least one magnetic sensor of observed magnetic susceptibility variation in the body.

46. The apparatus recited in claim 45, wherein said magnetic sensor attaches to a central region relative to said applied field coil.

47. The apparatus recited in claim 45, wherein said applied field coil comprises two parallel flat coils and a connecting circuit between said two parallel coils causing current to flow in identical directions at corresponding locations in said two flat coils, thereby simulating parallel uniform sheets of current.

48. The apparatus recited in claim 45, wherein said excitation field coil comprises at least two concentric coils and a connecting circuit between said at least two concentric coils causing current to flow in opposite directions, thereby canceling the effects of a magnetic field caused by current flowing through said applied field coil at a central region of said at least two concentric coils.

49. The apparatus recited in claim 45, wherein said detector assembly is multiple stacked applied field coils.

50. The apparatus recited in claim 45, wherein said at least one magnetic sensor is a magnetoresistive sensor, said sensor forms part of a Wheatstone bridge circuit and further comprises a means for compensating said magnetic sensor for locking an optimal operational state by applying a compensating electrical current from said compensating means thereby maintaining sensitivity of the apparatus.

51. The apparatus recited in claim 45, wherein said at least one magnetic sensor is a fluxgate sensor.

52. The apparatus recited in claim 45, wherein said at least one magnetic sensor is a magnetoinductive sensor.

53. The apparatus recited in claim 45, wherein said applied field coil comprises a coil on a cylindrical coilform and said at least one magnetic sensor comprises sensor coils axially spaced from said field coil on either side thereof on said coilform.

54. The apparatus recited in claim 53, wherein said sensor coils are oppositely around in a gradiometer configuration.

55. The apparatus recited in claim 53, wherein said coilform is formed of non-magnetic, non-metallic material.

56. The apparatus recited in claim 45, wherein said deformable material is water.

57. The apparatus recited in claim 45, wherein said deformable material is a gel.

58. An apparatus to eliminate background tissue response in an instrument for non-invasively measuring magnetic susceptibility variations in the body tissue of a patient to determine a compositional state in the body, said apparatus comprising:
 a non-conductive, non-magnetic, substantially rigid barrier; and
 a flexible membrane sealed to said barrier to form a container therewith, there being a deformable material within and occupying mast of the volume within said container, said material having a magnetic susceptibility substantially equivalent to that of the body tissue, said container being shaped and configured to fill in substantially all gaps between said barrier and the patient's body, said barrier and flexible membrane being configured to be substantially stationary with respect to the patient, and the amount of deformable material within said container remains constant when magnetic susceptibility variations in the patient's body tissue are being measured.

59. The apparatus recited in claim 58, wherein said deformable material is water.

60. The apparatus recited in claim 58, wherein said deformable material is a gel.

61. An apparatus for noninvasively measuring magnetic susceptibility variations in the body tissue of a patient to determine a compositional state in the body, the apparatus comprising:

a detector assembly that includes:
  at least one magnetic sensor and an applied field coil for generating a magnetic field, said applied field coil comprising at least two concentric circular spiral coils; and
  means for processing signals from said at least one magnetic sensor of observed magnetic susceptibility variations in body tissue;
 a non-conductive, non-magnetic, substantially rigid barrier;
 a flexible membrane sealed to said barrier to form a container therewith there being a deformable material within and occupying most of the volume within said container, said material having a magnetic susceptibility substantially equivalent to that of the body tissue, said container also being deformable to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and
 means for outputting data from said detector assembly corresponding to a compositional state in the body tissue;
 wherein the at least two concentric spiral coils have diameters and numbers of turns chosen so tat the magnetic field due to an inner concentric spiral coil cancels the magnetic field due to an outer concentric spiral coil in a region near the common center of the at least two concentric coils, thereby producing a zone of substantially zero magnetic field, and wherein the at least one magnetic sensor is placed in said zone of substantially zero magnetic field.

62. The apparatus recited in claim 61, wherein the apparatus further comprises displacement means for displacing the at least one magnetic sensor and the applied field coil simultaneously, thereby compensating for noise introduced to the sensed signals.

63. The apparatus recited in claim 62, wherein the displacement means operates between about one to about six inches.

64. The apparatus recited in claim 62, wherein the displacement means operates at between about 0.5 to about 10.0 Hertz.

65. The apparatus recited in claim 61, wherein the instrument further comprises an electrostatic shield located between the sensor and the sample to be measured.

66. The apparatus recited in claim 65, wherein the electrostatic shield is octagonal in shape.

67. The apparatus recited in claim 65, wherein the electrostatic shield comprises conducting material arranged in the form of thin strips connected in a branching pattern.

68. The apparatus recited in claim 67, wherein the strips are about 0.01 inches in width.

69. The apparatus recited in claim 68, wherein there is a gap of about 0.01 inches between each strip.

70. An apparatus for noninvasively measuring magnetic susceptibility variations in the body tissue of a patient to determine a compositional state in the body, the apparatus comprising:

a detector assembly that includes:
    at least one magnetic sensor and an applied field coil for generating a magnetic field;
    an alternating current signal generating source which connects to said applied field coil;
    means for processing signals from said at least one magnetic sensor of observed magnetic susceptibility variations in body tissues; and
    an electrostatic shield positioned between said at least one magnetic sensor and the sample to be measured;
a non-conductive, nan-magnetic, substantially rigid barrier;
a flexible membrane sealed to said barrier to form a container therewith, there being a deformable material within and occupying most of the volume within said container, said material having a magnetic susceptibility substantially equivalent to that of the body tissue, said container also being deformable to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and
means for outputting data from said detector assembly corresponding to a compositional state in the body.

71. The apparatus recited in claim 70, wherein said sensor comprises a sensing coil, said sensing coil comprising a relatively tightly wound and compact spool of wire.

72. The apparatus of claim 70, wherein said applied field coil comprises at least two concentric circular spiral coils.

73. The apparatus of claim 70, wherein the electrostatic shield comprises sheets of conductive material wrapped to provide continuous shielding of electrical fields, wherein overlapping layers of the wrapped material are insulated to prevent electrical contact therebetween.

74. The apparatus of claim 70, wherein the electrostatic shield comprises thin strips of conductive material, electrically connected in a branching configuration so that all parts of the shield are electrically connected but such that there are no conducting loops enclosing large areas.

75. The apparatus of claim 74, wherein the strips are less than about 0.015 inches in width.

76. The apparatus of claim 75, wherein the conductive strips are arranged on a thin substrate.

77. The apparatus of claim 76, wherein the thin substrate comprises a printed circuit board.

78. The apparatus of claim 77, wherein the conductive strips are placed on opposite sides of the printed circuit board in a staggered relationship so that the strips on one side cover the area where there are gaps between the strips on the other side.

79. An apparatus for noninvasively measuring magnetic susceptibility variations in the body tissue of a patient to determine a compositional state in the body, the apparatus comprising:
a detector assembly that includes:
    at least one magnetic sensor and an applied field coil for generating a magnetic field;
    a current signal generating source, which connects to said applied field coil; and
    means for processing signals from said at least one magnetic sensor of observed magnetic susceptibility variations in body tissue;
    a non-conductive, non-magnetic, substantially rigid barrier;
    a flexible membrane sealed to said barrier to form a container therewith, there being a deformable material within and occupying most of the volume within said container, maid material having a magnetic susceptibility substantially equivalent to that of the body tissue, said container being shaped and configured to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and
    means for outputting data from said detector assembly corresponding to a compositional state in the body;
    wherein the at least one magnetic sensor comprises a sensing coil and wherein the applied field coil and the sensing coil are mounted together in a rigid sensor unit, and
wherein the instrument is provided with displacement means for displacing the at least one magnetic sensor and the applied field coil simultaneously, thereby compensating for noise introduced to the sensed signals.

80. The apparatus of claim 79, wherein the applied field coil comprises at least two concentric circular spiral coils wherein the at least two concentric spiral coils have diameters and numbers of turns chosen so that the magnetic field due to an inner concentric spiral coil cancels the magnetic field due to an outer concentric spiral coil in a region near the common center of the at least two concentric coils, thereby producing a region of nearly zero magnetic field and wherein the at least one magnetic sensor is positioned in said region of nearly zero magnetic field.

81. The apparatus of claim 79, wherein the sensing coil and applied field coil are enclosed in an electrostatic shield.

82. The apparatus of claim 81, wherein the electrostatic shield comprises sheets of conductive material wrapped to provide continuous shielding of electrical fields, wherein overlapping layers of the wrapped material are insulated to prevent electrical contact therebetween.

83. The apparatus of claim 81, wherein the electrostatic shield comprises thin strips of conductive material, electrically connected in a branching configuration so that all parts of the shield are electrically connected but such that there are no conducting loops enclosing large areas.

84. The apparatus of claim 83, wherein the strips are less than about 0.015 inches in width.

85. The apparatus of claim 84, wherein the conductive strips are arranged on a thin substrate.

86. The apparatus of claim 85, wherein the thin substrate comprises a printed circuit board.

87. The apparatus of claim 86, wherein the conductive strips are placed on opposite sides of the printed circuit board in a staggered relationship so that the strips on one side cover the area where there are gaps between the strips on the other side.

88. An apparatus for noninvasively measuring magnetic susceptibility variations in the body tissue of a patient to determine a compositional state in the body, the apparatus comprising:
a detector assembly that includes:
    at least one magnetic sensor and an applied field coil for generating a magnetic field;

a current signal generating source, which connects to said applied field coil; and means for processing signals from said at least one magnetic sensor of observed magnetic susceptibility variations in body tissue;

a non-conductive non-magnetic, substantially rigid barrier;

a flexible membrane sealed to said barrier to form a container therewith, there being a deformable material within and occupying most of the volume within said container, said material having a magnetic susceptibility substantially equivalent to that of the body tissue, said container being shed and configured to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and means for outputting data from said detector assembly corresponding to a compositional state in the body;

wherein the at least one magnetic sensor comprises a sensor unit, said sensor unit comprising two sensing coils connected in series, equal in area, but oppositely wound, and oppositely spaced from the applied field coil on a cylindrical coilform in a first-order gradiometer configuration;

wherein the sensing coils and applied field coil have areas and geometric locations chosen so as to cancel out the detected signal due to the applied magnetic field;

wherein the applied field coil and the sensing coils are mounted together in said sensor unit, and wherein the instrument is provided with means for displacing the sensor unit, thereby compensating for the effects of temperature drift; and wherein the instrument further comprises an electrostatic shield between the sensing coils and the body tissue to be measured.

89. The apparatus of claim 88, wherein the means for displacing the sensing unit displaces the sensor unit toward and away from the body tissue.

90. The apparatus of claim 88, wherein the means for displacing to sensing unit displaces the sensor unit laterally with respect to the body tissue.

91. The apparatus of claim 88, wherein the applied field coil comprises a circular loop, and the sensing coils comprise a first order gradiometer, said gradiometer consisting of two oppositely wound coils of equal area, connected in series and located symmetrically with respect to the applied field coil so as to cancel out the detected signal due to the applied field.

92. The apparatus of claim 91, wherein the sensing coils are unequal in area, and their locations wit respect to the applied field coil are chosen so as to cancel out the detected signal due to the applied field.

93. The apparatus of claim 88, wherein the applied field coil is a first order or higher gradiometer, and the sensing coils are configured at second order or higher gradiometers.

94. A method for noninvasive determination of magnetic susceptibility variations in a patient by measuring magnetic susceptibilities of selected body tissue of the patient, the method comprising:

providing an instrument which includes at leant one magnetic sensor and an applied field coil;

positioning on the patient a flexible bag substantially filled with deformable material having a magnetic susceptibility substantially similar to that of the body tissue, said bag being attached to a substantially rigid barrier, the barrier being spaced a predetermined distance from the patient by the deformable material filled bag, which predetermined distance remains substantially constant during a measuring sequence, the amount of deformable material in the flexible bag remaining constant during a measuring sequence, the instrument being moved with respect to the barrier during the measuring sequence;

positioning the instrument external to the patient in proximity to the tissue of interest and adjacent the barrier;

supplying the applied field coil with current thereby applying a magnetic field to the tissue of interest;

scanning the at least one magnetic sensor along the rigid barrier to generate a map of susceptibility variations of the underlying body tissues; and outputting data corresponding to the magnetic susceptibility variations in the tissue.

95. A method for noninvasive determination of magnetic susceptibility variation in a patient by measuring magnetic susceptibilities of selected body tissue of the patient, the method comprising:

providing an instrument which includes at least one magnetic sensor and an applied field coil;

positioning on the patient a flexible bag substantially filled with a first amount of deformable material having a magnetic susceptibility substantially similar to that of the body tissue, said bag being attached to a substantially rigid barrier to form a container having a first volume, the barrier being spaced a first predetermined distance from the patient by the deformable material filled bag;

positioning the instrument external to the patient in proximity to the tissue of interest and adjacent the barrier;

supplying the applied field coil with current thereby applying a magnetic field to the tissue of interest;

periodically displacing the instrument with respect to the barrier, sensing a response from the tissue of interest with the instrument;

outputting data corresponding to the magnetic susceptibility variation in the tissue; ten moving the instrument and the substantially rigid barrier simultaneously with respect to the patient, the barrier being thereby spaced from the patient by a second predetermined distance and changing the container to have a second volume, the second volume being filled with a second amount of deformable material;

repeating the supplying step, the periodically displacing step, the sensing step and outputting step; and subtracting the susceptibility measurement observed after the moving step from the susceptibility measurement observed before the moving step.

96. The method according to claim 95, wherein said displacement is between about one to about six inches.

97. The method according to claim 95, wherein the displacement means operates between about 0.5 to about 10.0 Hertz.

98. The method according to claim 95, wherein the moving step permits the drift in the sensor output to be subtracted out more effectively.

99. The method according to claim 95, wherein said displacement and moving occur simultaneously.

100. An apparatus for noninvasively measuring magnetic susceptibility variations in the body tissue of a patient to determine a compositional state in the body, the apparatus comprising:
- a detector assembly that includes:
  - at least one magnetic sensor and an applied field coil for generating a magnetic field;
  - a signal refinement means adjustably positioned with respect to the sensor;
  - a current signal generating source which connects to said applied field coil; and
  - means for processing signals from said at least one magnetic sensor of observed magnetic susceptibility variations in body tissue;
- a non-conductive, non-magnetic, substantially rigid barrier;
- a flexible membrane sealed to said barrier to form a container therewith, there being a deformable material within and occupying moat of the volume within said container, said material having a magnetic susceptibility substantially equivalent to that of the body tissue, said container being shaped and configured to fill in substantially all gaps between said barrier and the patient's body, said barrier being substantially stationary with respect to the patient and the amount of deformable material within said container being constant when magnetic susceptibility variations in the patient's body tissue are measured, the patient remains stationary and said detector assembly moves with respect to said barrier when the measurements are being made; and
- means for outputting data from said detector assembly corresponding to a compositional state in the body tissue;
- wherein said applied field coil is designed to produce a region of nearly zero magnetic field and said sensor is positioned in said region of nearly zero magnetic field and wherein adjustment of said signal refinement means improves cancellation of the applied field at the sensor location.

101. The apparatus of claim 100, wherein said signal refinement means is selected from the group consisting of a balance coil, ferromagnetic tabs on the coilform and an electronic imbalance sensing and compensating means.

102. The apparatus of claim 101, wherein said balance coil is connected in series with the applied field coil.

103. The apparatus of claim 101, wherein said balance coil is adjustable on an axis parallel to a longitudinal axis of the sensor.

104. The apparatus of claim 101, wherein the balance coil comprises a plurality of turns of wire on a non-metallic, non-magnetic cylindrical coilform.

105. The apparatus of claim 104, wherein the plurality of turns of wire is about 10 to about 20 and the cylindrical coilform diameter is about 1 to about 1.5 inches.

* * * * *